US008349846B2

(12) United States Patent
Lingam et al.

(10) Patent No.: US 8,349,846 B2
(45) Date of Patent: Jan. 8, 2013

(54) FUSED PYRIMIDINE DERIVATIVES AS TRPV3 MODULATORS

(75) Inventors: V S. Prasadarao Lingam, Koparkhairane (IN); Abraham Thomas, Sanpada (IN); Dattaguru Anandrao More, Kolhapur (IN); Javed Yusuf Khatik, Kausa-Mumbra (IN); Neelima Khairatkar-Joshi, Pachpakhadi (IN); Vidya Ganapati Kattige, Thane (W) (IN)

(73) Assignee: Glenmark Pharmaceuticals, S.A., La Chaux-de-Fonds (CH)

( * ) Notice: Subject to any disclaimer, the term of this patent is extended or adjusted under 35 U.S.C. 154(b) by 211 days.

(21) Appl. No.: 12/811,975

(22) PCT Filed: Jan. 7, 2009

(86) PCT No.: PCT/IN2009/000025
§ 371 (c)(1),
(2), (4) Date: Jul. 7, 2010

(87) PCT Pub. No.: WO2009/109987
PCT Pub. Date: Sep. 11, 2009

(65) Prior Publication Data
US 2010/0292254 A1 Nov. 18, 2010

Related U.S. Application Data

(60) Provisional application No. 61/028,770, filed on Feb. 14, 2008, provisional application No. 61/048,276, filed on Apr. 28, 2008.

(30) Foreign Application Priority Data

Jan. 11, 2008 (IN) .............................. 82/MUM/2008
Mar. 18, 2008 (IN) ........................... 548/MUM/2008
Apr. 4, 2008 (IN) ........................... 798/MUM/2008

(51) Int. Cl.
*A61K 31/519* (2006.01)
(52) U.S. Cl. ................. 514/259.4; 514/259.41; 544/282
(58) Field of Classification Search .................... 544/282
See application file for complete search history.

(56) References Cited

U.S. PATENT DOCUMENTS

| 4,223,031 | A | | 9/1980 | Covington et al. |
| 4,341,780 | A | * | 7/1982 | Doria et al. ................... 514/257 |
| 4,444,773 | A | | 4/1984 | Doria et al. |
| 4,537,962 | A | | 8/1985 | Doria et al. |
| 4,551,457 | A | | 11/1985 | Doria et al. |
| 4,558,046 | A | | 12/1985 | Doria et al. |
| 4,609,660 | A | | 9/1986 | Doria et al. |
| 5,204,352 | A | | 4/1993 | Sundberg et al. |
| 5,703,085 | A | | 12/1997 | Suzuki et al. |
| 5,804,583 | A | | 9/1998 | Salimbeni et al. |
| 6,323,208 | B1 | | 11/2001 | Chenard et al. |
| 6,492,383 | B1 | | 12/2002 | Munchhof et al. |
| 7,625,838 | B2 | | 12/2009 | Alterman et al. |
| 7,842,703 | B2 | | 11/2010 | Gharat et al. |
| 2006/0040944 | A1 | | 2/2006 | Gosselin et al. |
| 2006/0052596 | A1 | | 3/2006 | Muller et al. |
| 2007/0179164 | A1 | | 8/2007 | Chong et al. |
| 2007/0219222 | A1 | | 9/2007 | Moran et al. |
| 2007/0249647 | A1 | | 10/2007 | Vander Jagt et al. |
| 2008/0145819 | A1 | | 6/2008 | Bottcher |
| 2008/0194616 | A1 | | 8/2008 | Liu et al. |
| 2010/0009969 | A1 | | 1/2010 | Denonne et al. |
| 2010/0152209 | A1 | | 6/2010 | Chong et al. |

FOREIGN PATENT DOCUMENTS

| JP | 07242666 A | 9/1995 |
| WO | 02/04444 A3 | 1/2002 |
| WO | 2006/065686 A2 | 6/2006 |
| WO | 2008/001101 A2 | 1/2008 |

OTHER PUBLICATIONS

Jia et al. Role of TRPV receptors in respiratory diseases. 2007. Biochimica et Biophysica Acta, 1772, 915-927.*
Adreani et al., Dihydropyridines bearing imadazo [2, 1-b] thiazole; Eur. J. of Med. Chem, 1997, 32 (2), 151-157.
Cesur Z., et al., Synthesis and Antimycobacterial Activity of New Imidazo [2, 1-b], Thiazole Derivatives Eur. J. Med. Chem., 1994, 29, 981-983.
Foulis, M.J., et al., J. Med., Chem., 1971, 28, 1075.
Hu, H. Z., et al. J. Biol. Chem. (2004), 279, 35741-35748.
Hu, H. Z. et al, Journal of Cellular Physiology, (2006), 208, 201-212.
Huff, et al. Org. Synth. (1997), 75, 53-56.
Laneri, S., et al., Eur. J. Med., Chem., 1998, 33, 163-170.
Miyaura; Suzuki, A., Chem. Rev. (1995), 95, 2457-2483.
Passarotti, C.M., et al., Synthesis and antiinflammatory Activity of Some Thiazolo (3,2-1) pyrimidine Derivatives Containing a Thioether Group, vol. 134, No. 11, Jan. 1, 1995; pp. 639-643.
Peterlin-Masic L. et al., J. Het. Chem., 2000, 37, 95-101.

(Continued)

*Primary Examiner* — Brian McDowell
(74) *Attorney, Agent, or Firm* — Gillman Pergament LLP; Edward D. Pergament; Milagros A. Cepeda

(57) ABSTRACT

The present invention related to fused pyrimidine derivatives, which are useful as Transient Receptor Potential Vanilloid 3 (TRPV3) receptors, methods of treating diseases, disorders, conditions modulated by TRPV3. The present invention having the formula (I) and its pharmaceutically acceptable salts thereof, and its processes thereof, wherein all variables are as described herein.

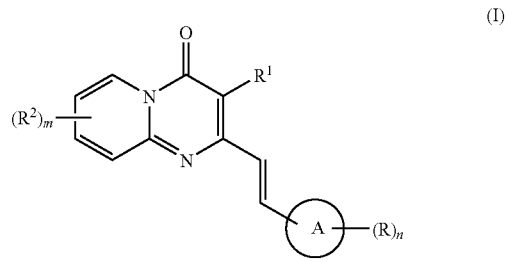

(I)

25 Claims, No Drawings

OTHER PUBLICATIONS

Philipova, P. et al., J. Het. Chem., 2006, 43, 1057.
Russian Chemical Bulletin, 1999, vol. 48(6) pp. 1143.
Starrett J. E. et al., J. Med. Chem. 1989, 32, 2204.
Tanaka, K. et al., J. Het. Chem., 1991, 28, 907.
Toth, A. et al. Life Sciences (2003), 73, 487-498.
Supplemental European Search Report dated Feb. 2, 2012 for corresponding International Patent Application No. PCT/IN2009000025.
Doria, Gianfederico et al.: "Antiallergic agents. VI. Sustituted 2-trans-ethenyl-4-oxo-4 H-pyrido [1,2-a] pyrimidine-7-carboxylic acids", European Journal of Medicinal Chemistry, 18 (3), Jan. 6, 1983, pp. 227-232.

Yale, Harry L. et al.: "The Reaction of Aromatic Aldehydes with Methyl-substituted 4H-Pyrido[1,2-a] pyrimidin-4-ones", Journal of Heterocyclic Chemistry, 13 (4), Aug. 1976, pp. 869-871.
Passarotti, C. et al.: "Synthesis of New 2-(2-Phenylethenyl)-4-OCO-4H-Pyrido[1.2-a] Pyrimidine-7-Carboxylic Acids", Farmaco, Edizione Scientifica, 39 (10), Feb. 17, 1984, pp. 837-845.
Supplemental European Search Research dated Feb. 2, 2012 for corresponding International Patent Application No. PCT/IN2009000025.

\* cited by examiner

FUSED PYRIMIDINE DERIVATIVES AS TRPV3 MODULATORS

RELATED APPLICATIONS

This application claims the benefit of Indian Patent Application No. 82/MUM/2008 filed on Jan. 11, 2008, and 548/MUM/2008 filed on Mar. 18, 2008, and 798/MUM/2008 filed on Apr. 4, 2008, U.S. Provisional Application No. 61/028,770, filed on Feb. 14, 2008, and 61/048,276, filed on Apr. 28, 2008 all of which are hereby incorporated by reference.

TECHNICAL FIELD

The present patent application relates to fused pyrimidine derivatives with Transient Receptor Potential Vanilloid 3 (TRPV3) activity.

BACKGROUND

Movement of ions across cellular membranes is carried out by specialized proteins. TRP channels are one large family of non-selective cation channels that function to help regulate ion flux and membrane potential. TRP channels are subdivided into 6 sub-families including the TRPV family. TRPV3 is a member of the TRPV class of TRP channels.

TRPV3 is a calcium permeable channel, specifically a calcium permeable nonselective cation channel. In addition to calcium ions, TRPV3 channels are permeable to other cations, for example sodium. Thus, TRPV3 channels modulate membrane potential by modulating the flux of cations such as calcium and sodium ions. TRPV3 receptors are mechanistically distinct from voltage-gated calcium channels. Generally, voltage-gated calcium channels respond to membrane depolarization and open to permit an influx of calcium from the extracellular medium that result in an increase in intracellular calcium levels or concentrations. In contrast, TRP channels which are non-selective, long lasting, produce more prolonged changes in ion concentration and are ligand gated (such as 2-aminoethoxydiphenyl borate [2-APB], heat, and vanilloids). These mechanistic differences are accompanied by structural differences among voltage-gated and TRP channels. Thus, although many diverse channels act to regulate ion flux and membrane potential in various cell types and in response to numerous stimuli, it is important to recognize the significant structural, functional, and mechanistic differences among different classes of ion channels.

TRPV3 proteins are thermosensitive channels expressed in skin cells (Peier et al. *Science* (2002), 296, 2046-2049) and dorsal root ganglion, trigeminal ganglion, spinal cord and brain (Xu et al. *Nature* (2002), 418, 181-185; Smith et al. *Nature* (2002), 418, 186-188). In a keratinocyte cell line, stimulation of TRPV3 leads to release of inflammatory mediators including interleukin-1. Thus TRPV3 may also play an important role in regulating inflammation and pain that results from the release of inflammatory stimuli. Particular TRPV3 proteins that may be used in screening assays, as described herein, to identity compounds that modulate a function of TRPV3 include, but are not limited to human TRPV3, mouse TRPV3, rat TRPV3 and *Drosophila* TRPV3. US 2004/0009537 (the '537 application) disclosed sequences corresponding to human, mouse, and *Drosophila* TRPV3. For example, SEQ ID Nos 106 and 107 of the '537 application correspond to the human nucleic acid and amino acid sequences, respectively. SEQ ID Nos 108 and 109 of the '537 application correspond to the mouse nucleic acid and amino acid sequences, respectively.

TRPV3 function has been basically implicated in the reception and transduction of pain. Accordingly, it would be desirable to identify and make compounds that can modulate one or more functions of TRPV3.

WO 2007/056124 and WO 2006/017995 disclose TRPV3 modulators, in particular antagonists, for treatment of various diseases mediated TRPV3.

WO 2006/065686 and WO 2007/042906 disclose benzopyran derivatives.

In efforts to discover better analgesics, there still exists a need for therapeutic treatment of diseases, conditions and/or disorders modulated by TRPV3.

SUMMARY

The present patent application relates to compounds of the formula (I):

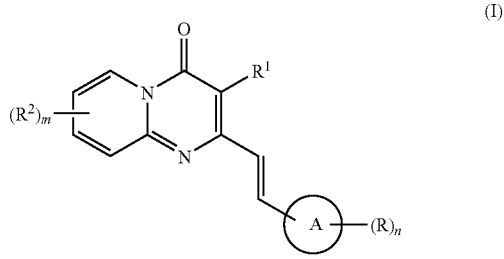

wherein, ring A is aryl, heteroaryl or heterocyclic group;

R is nitro, cyano, halogen, —OR$^a$, substituted or unsubstituted alkyl, haloalkyl, substituted or unsubstituted cycloalkyl, substituted or unsubstituted aryl, substituted or unsubstituted heterocyclic group or substituted or unsubstituted heteroaryl;

R$^1$ is nitro, cyano, halogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclic group, —NR$^3$R$^4$, —C(O)—R$^3$, —C(O)OR$^3$, —C(O)NR$^3$R$^4$, —S(O)$_p$NR$^3$R$^4$ or —S(O)$_p$R$^3$; wherein substituents of aryl, heteroaryl or heterocyclic group are independently selected from halogen, nitro, cyano, —COOH, —C(O)—R$^3$, —NHC(O)—R$^3$, —OR$^a$, substituted or unsubstituted alkyl, linear or branched chain alkyl, haloalkyl, thioalkyl or substituted or unsubstituted cycloalkyl;

R$^2$ is hydrogen, nitro, cyano, halogen, —OR$^a$, substituted or unsubstituted alkyl, substituted or unsubstituted cycloalkyl, substituted or unsubstituted cycloalkenyl, substituted or unsubstituted aryl, substituted or unsubstituted heteroaryl, substituted or unsubstituted heterocyclic group, —NR$^3$R$^4$, —C(O)—R$^3$, —C(O)O—R$^3$, —C(O)NR$^3$R$^4$, —S(O)$_p$NR$^3$R$^4$ or —S(O)$_p$R$^3$;

each occurrence of R$^a$ is independently selected from the group consisting of hydrogen, substituted or unsubstituted alkyl, haloalkyl, substituted or unsubstituted alkenyl, substituted or unsubstituted cycloalkyl, substituted or unsubstituted aryl, substituted or unsubstituted heteroaryl, substituted or unsubstituted heterocyclic group, substituted or unsubstituted cycloalkylalkyl, substituted or unsubstituted arylalkyl, substituted or unsubstituted heteroarylalkyl or substituted or unsubstituted heterocyclylalkyl;

each occurrence of R$^3$ and R$^4$ are independently hydrogen, —OR$^a$, substituted or unsubstituted alkyl, substituted or unsubstituted alkenyl, substituted or unsubstituted cycloalkyl, substituted or unsubstituted cycloalkylalkyl, substituted or unsubstituted cycloalkenyl substituted or unsubstituted aryl, substituted or unsubstituted arylalkyl, substituted or unsubstituted heteroaryl, substituted or unsubstituted heteroarylalkyl, substituted or unsubstituted heterocyclic group or substituted or unsubstituted heterocyclylalkyl;

'm' is an integer selected from 0 to 4;
'n' is an integer selected from 0 to 5;
'p' is an integer selected from 0 to 2.

It should be understood that the formula (I) structurally encompasses all stereoisomers, enatiomers and diastereomers and pharmaceutically acceptable salt that may be contemplated from the chemical structure of the genus described herein.

According to one embodiment, ring A is aryl.

According to one embodiment, ring A is heteroaryl. In this embodiment ring A is thienyl or pyridine; and 'n' is 0.

According to one embodiment, ring A is heterocyclic group. In this embodiment ring A is benzodioxole; and 'n' is 0.

According to one embodiment, 'm' is 0.

According to one embodiment, $R^1$ is substituted or unsubstituted aryl.

According to one embodiment, $R^1$ is substituted or unsubstituted heteroaryl.

Another preferred embodiment of the present invention is a compound of Formula (II),

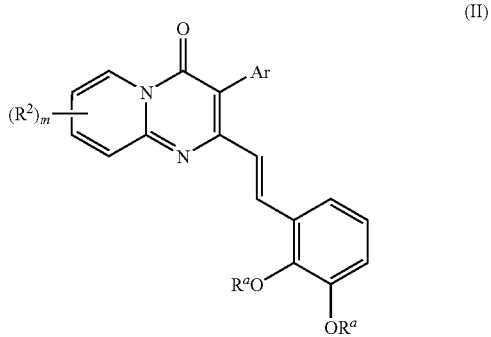

(II)

wherein,

Ar is substituted or unsubstituted aryl, substituted or unsubstituted heteroaryl or substituted or unsubstituted heterocyclic group; wherein substituents of aryl, heteroaryl or heterocyclic group are independently selected from halogen, nitro, cyano, —COOH, —C(O)—$R^3$, —NHC(O)—$R^3$, —$OR^a$, substituted or unsubstituted alkyl, linear or branched chain alkyl, haloalkyl, thioalkyl or substituted or unsubstituted cycloalkyl;

$R^2$ is hydrogen, nitro, cyano, halogen, —$OR^a$, substituted or unsubstituted alkyl, substituted or unsubstituted cycloalkyl, substituted or unsubstituted cycloalkenyl, substituted or unsubstituted aryl, substituted or unsubstituted heteroaryl, substituted or unsubstituted heterocyclic group, —$NR^3R^4$, —C(O)—$R^3$, —$C(O)OR^3$, —$C(O)NR^3R^4$, —$S(O)_pNR^3R^4$ or —$S(O)_pR^3$;

each occurrence of $R^a$ is independently selected from the group consisting of hydrogen, substituted or unsubstituted alkyl, haloalkyl, substituted or unsubstituted alkenyl, substituted or unsubstituted cycloalkyl or unsubstituted aryl, substituted or unsubstituted heteroaryl, substituted or unsubstituted heterocyclic group, substituted or unsubstituted cycloalkylalkyl, substituted or unsubstituted arylalkyl, substituted or unsubstituted heteroarylalkyl or substituted or unsubstituted heterocyclylalkyl;

each occurrence of $R^3$ and $R^4$ are independently hydrogen, —$OR^a$, substituted or unsubstituted alkyl, substituted or unsubstituted alkenyl, substituted or unsubstituted cycloalkyl, substituted or unsubstituted cycloalkylalkyl, substituted or unsubstituted cycloalkenyl substituted or unsubstituted aryl, substituted or unsubstituted arylalkyl, substituted or unsubstituted heteroaryl, substituted or unsubstituted heteroarylalkyl, substituted or unsubstituted heterocyclic group or substituted or unsubstituted heterocyclylalkyl;

'm' is an integer selected from 0 to 4;
'p' is an integer selected from 0 to 2.

It should be understood that the formula (II) structurally encompasses all stereoisomers, enatiomers and diastereomers and pharmaceutically acceptable salt that may be contemplated from the chemical structure of the genus described herein.

According to one embodiment, Ar is unsubstituted aryl. In this embodiment Ar is unsubstituted phenyl.

According to one embodiment, Ar is substituted aryl. In this embodiment Ar is substituted phenyl, wherein substituents one or more are independently selected from halogen (for eg., F, Cl or Br), hydroxyl, cyano, linear or branched chain alkyl, haloalkyl (for eg., trifluoromethyl), linear or branched chain alkoxy (for eg., methoxy, iso-propyloxy), thioalkyl (for eg., —$SCH_3$), haloalkoxy (for eg., trifluoromethoxy), —COOH, nitro, acyl, or alkanoylamino (for eg., —$NHCOCH_3$).

According to one embodiment, Ar is substituted or unsubstituted heteroaryl.

According to one embodiment, Ar is substituted heteroaryl. In this embodiment Ar is substituted pyridine, wherein substituent(s) is halogen for eg., F, Cl or Br.

According to one embodiment, Ar is unsubstituted heteroaryl. In this embodiment Ar is pyridine or quinoline.

According to one embodiment, Ar is substituted or unsubstituted heterocyclic group. In this embodiment Ar is benzodioxole or benzodioxine.

According to one embodiment, $R^a$ is independently selected from alkyl (for eg., methyl, propyl, n-butyl, n-pentyl or n-hexyl), cycloalkyl (for eg., cyclopentyl), cycloalkylalkyl (for eg., cyclopropylmethyl) or dialkylaminoalkyl (for eg., —$CH_2CH_2N(CH_3)_2$.

According to one embodiment, $R^2$ is halogen (for eg., F, Cl or Br), alkyl (for eg., methyl) or alkoxy (for eg., methoxy); and 'm' is 1.

Below are the representative compounds, which are illustrative in nature only and are not intended to limit to the scope of the invention.

2-[(E)-2-(4-Chlorophenyl)vinyl]-3-phenyl-4H-pyrido[1,2-a]pyrimidin-4-one (Compound No 1), 2-{(E)-2-(Pyridin-3-yl)vinyl}-3-(4-trifluoromethyl)phenyl-4H-pyrido[1,2-a]pyrimidin-4-one (Compound No 2), 2-[(E)-2-(2-Thienyl)vinyl]-3-[4-(trifluoromethyl)phenyl]-4H-pyrido[1,2-a]pyrimidin-4-one (Compound No 3), 2-[(E)-2-(1,3-Benzodioxol-4-yl)vinyl]-3-[4-(trifluoromethyl)phenyl]-4H-pyrido[1,2-a]pyrimidin-4-one (Compound No 4), 4-{2-[(E)-2-[2-(Cyclopentyloxy)-3-methoxyphenyl)vinyl]-4-oxo-4H-pyrido[1,2-a]pyrimidin-3-yl}benzonitrile (Compound No 5), 2-[(E)-2-[(3-Methoxy-2-propoxyphenyl)vinyl]-3-[4-(trifluoromethyl)phenyl]-4H-pyrido[1,2-a]pyrimidin-4-one (Compound No 6), 4-{2-[(E)-2-[(3-Methoxy-2-propoxyphenyl)vinyl]-4-oxo-4H-pyrido[1,2-a]pyrimidin-3-yl}benzonitrile (Compound No 7), 2-[(E)-2-[(2-Butoxy-3-methoxyphenyl)vinyl]-3-[4-(trifluoromethyl)phenyl]-4H-pyrido[1,2-a]pyrimidin-4-one (Compound No 8), 2-[(E)-2-[2-Butoxy-3-methoxyphenyl)vinyl]-3-[4-(trifluoromethoxy)phenyl]-4H-pyrido[1,2-a]pyrimidin-4-one (Compound No 9), 4-{2-[(E)-2-[(2-Butoxy-3-methoxyphenyl)vinyl]-4-oxo-4H-pyrido[1,2-a]pyrimidin-3-yl}benzonitrile (Compound No 10), 2-[(E)-2-[(3-Methoxy-2-pentyloxyphenyl)vinyl]-3-[4-(trifluoromethyl)phenyl]-4H-pyrido[1,2-a]pyrimidin-4-one (Compound No 11), 4-{2-[(E)-2-[3-Methoxy-2-pentyloxyphenyl)vinyl]-4-oxo-4H-pyrido[1,2-a]pyrimidin-3-yl}benzonitrile (Compound No 12), 2-[(E)-2-[(2-Hexyloxy-3-methoxyphenyl)vinyl]-3-[4-(trifluoromethyl)phenyl]-4H-pyrido[1,2-a]pyrimidin-4-one (Compound No 13), 4-{2-[(E)-2-[(2-Hexyloxy-3-methoxyphenyl)vinyl]-4-oxo-4H-pyrido[1,2-a]pyrimidin-3-yl}benzonitrile (Compound No 14), 2-[(E)-2-{2-[2-(Dimethylamino)ethoxy]-3-methoxyphenyl]vinyl}-3-(4-trifluoromethyl phenyl)-4H-pyrido[1,2-a]pyrimidin-4-one hydrochloride (Compound No 15), 2-{(E)-2-[2-(Cyclopropylmethoxy)-3-methoxyphenyl]vinyl}-3-phenyl-4H-pyrido[1,2-a]-pyrimidin-4-one (Compound No 16), 2-[(E)-2-[(2-Cyclopropylmethoxy-3-methoxyphenyl)vinyl]-3-[4-(trifluoromethyl)phenyl]-4H-pyrido[1,2-a]pyrimidin-4-one (Compound No 17), 2-[(E)-2-[(2-Cyclopropylmethoxy-3-methoxyphenyl)vinyl]-3-[4-(trifluoro-methoxy)phenyl]-4H-pyrido[1,2-a]pyrimidin-4-one (Compound No 18), 4-{2-[(E)-2-[(2-Cyclopropylmethoxy-3-methoxyphenyl)vinyl]-4-oxo-4H-pyrido[1,2-a]pyrimidin-3-yl}benzonitrile (Compound No 19), 2-{(E)-2-[2-(Cyclopentyloxy)-3-methoxyphenyl]vinyl}-3-phenyl-4H-pyrido[1,2-a]-pyrimidin-4-one (Compound No 20), 2-{(E)-2-[2-(Cyclopentyloxy-3-methoxy)phenyl]vinyl}-3-(3,5-difluoro)phenyl-4H-pyrido[1,2-a]pyrimidin-4-one (Compound No 21), 2-{(E)-2-[(2-Cyclopentyloxy-3-methoxy)phenyl]vinyl}-3-(3-trifluoromethyl)phenyl-4H-pyrido[1,2-a]pyrimidin-4-one (Compound No 22), 2-{(E)-2-[2-(Cyclopentyloxy)-3-methoxyphenyl]vinyl}-3-(4-trifluoromethyl)phenyl-4H-pyrido[1,2-a]pyrimidin-4-one (Compound No 23), 2-{(E)-2-[(2-Cyclopentyloxy-3-methoxy)phenyl]vinyl}-3-(4-trifluoromethoxy)phenyl-4H-pyrido[1,2-a]pyrimidin-4-one (Compound No 24), 2-{(E)-2-[2-(Cyclopentyloxy-3-methoxy)phenyl]vinyl}-3-(3-hydroxy)phenyl-4H-pyrido[1,2-a]-pyrimidin-4-one (Compound No 25), 2-{(E)-2-[(2-Cyclopentyloxy-3-methoxy)phenyl]vinyl}-3-(3-methoxy)phenyl-4H-pyrido[1,2-a]pyrimidin-4-one (Compound No 26), 3-(3-Isopropoxyphenyl)-2-[(E)-2-(2-cyclopentyloxy-3-methoxy)phenylvinyl]-4H-pyrido[1,2-a]pyrimidin-4-one (Compound No 27), 4-{2-[(E)-2-(2-Cyclopentyloxy-3-methoxyphenyl)vinyl]-4-oxo-4H-pyrido[1,2-a]pyrimidin-3-yl}benzonitrile (Compound No 28), 4-{4-Oxo-2-[(E)-2-(2-cyclopentyloxy-3-methoxy)phenylvinyl]-4H-pyrido[1,2-a]pyrimidin-3-yl}benzoic acid (Compound No 29), 2-{(E)-2-[(2-Cyclopentyloxy)-3-methoxyphenyl]vinyl}-3-(4-nitro)phenyl-4H-pyrido[1,2-a]pyrimidin-4-one (Compound No 30), N-(3-{2-[(E)-2-(2-Cyclopentyloxy-3-methoxy)phenylvinyl]-4-oxo-4H-pyrido[1,2-a]pyrimidin-3-yl}phenyl)acetamide (Compound No 31), N-(4-{2-[(E)-2-(2-Cyclopentyloxy-3-methoxy)phenylvinyl]-4-Oxo-4H-pyrido[1,2-a]pyrimidin-3-yl}phenyl)acetamide (Compound No 32), 3-(4-Acetylphenyl)-2-[(E)-2-(2-cyclopentyloxy-3-methoxy)phenylvinyl]-4H-pyrido[1,2-a]pyrimidin-4-one (Compound No 33), 2-{(E)-2-[(2-Cyclopentyloxy-3-methoxy)phenyl]vinyl}-3-(4-thiomethyl)phenyl-4H-pyrido[1,2-a]pyrimidin-4-one (Compound No 34), 2-{(E)-2-[2-(Cyclopentyloxy)-3-methoxyphenyl]vinyl}-3-pyridin-4-yl-4H-pyrido[1,2-a]-pyrimidin-4-one (Compound No 35), 2-{(E)-2-[2-(Cyclopentyloxy-3-methoxy)phenyl]vinyl}-3-(6-fluoro)pyridin-3-yl-4H-pyrido[1,2-a]pyrimidin-4-one (Compound No 36), 3-(1,3-Benzodioxol-5-yl)-2-[(E)-2-(2-cyclopentyloxy-3-methoxy)phenylvinyl]-4H-pyrido[1,2-a]pyrimidin-4-one (Compound No 37), 2-[(E)-2-(2-Cyclopentyloxy-3-methoxyphenyl)vinyl]-3-(2,3-dihydro-1,4-benzodioxin-6-yl)-4H-pyrido[1,2-a]pyrimidin-4-one (Compound No 38), 2-[(E)-2-(2-Cyclopentyloxy-3-methoxy)phenylvinyl]-3-quinolin-6-yl-4H-pyrido[1,2-a]pyrimidin-4-one (Compound No 39), 2-{(E)-2-[(2-Cyclopentyloxy-3-methoxy)phenyl]vinyl}-9-methyl-3-(4-trifluoromethyl)phenyl-4H-pyrido[1,2-a]pyrimidin-4-one (Compound No 40), 4-{2-[(E)-2-(2-Cyclopentyloxy-3-methoxyphenyl)vinyl]-9-methoxy-4-oxo-4H-pyrido[1,2-a]pyrimidin-3-yl}benzonitrile (Compound No 41), 4-{7-Chloro-2-[(E)-2-[(2-Cyclopropylmethoxy-3-methoxyphenyl)vinyl]-4-oxo-4H-pyrido[1,2-a]pyrimidin-3-yl}benzonitrile (Compound No 42) and 4-{7-Chloro-2-[(E)-2-(2-cyclopentyloxy-3-methoxy)phenylvinyl]-4-oxo-4H-pyrido[1,2-a]pyrimidin-3-yl}benzonitrile (Compound No 43) or an analog, tautomer, regiomer, stereoisomer, enantiomer, diastereomer or pharmaceutically acceptable salt thereof compounds 1 to 43 are also contemplated.

The present patent application also provides a pharmaceutical composition that includes at least one compound of described herein and at least one pharmaceutically acceptable excipient (such as a pharmaceutically acceptable carrier or diluent). Preferably, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, paper or other container.

The compounds and pharmaceutical compositions described herein are useful in the treatment of diseases, conditions and/or disorders modulated by TRPV3 receptors.

The present patent application further provides a method of treating a disease, condition and/or disorder modulated by TRPV3 receptors in a subject in need thereof by administering to the subject one or more compounds described herein in the amount effective to cause inhibition of such receptor.

Also provided herein are processes for preparing compounds described herein.

DETAILED DESCRIPTION

The present a patent application provides fused pyrimidine compounds, which may be used as TRPV3 modulators, and processes for the synthesis of these compounds. Pharmaceutically acceptable salts, enantiomers, diastereomers, of these compounds that may have the same type of activity are also provided. Pharmaceutical compositions containing the described compounds together with pharmaceutically acceptable carriers, excipients or diluents, which can be used for the treatment of diseases, condition and/or disorders mediated by TRPV3 are further provided.

The following definitions apply to the terms as used herein:

The terms "halogen" or "halo" includes fluorine, chlorine, bromine, or iodine

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms.

The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl(allyl), iso-propenyl, 2-methyl-1-propenyl, 1-butenyl, and 2-butenyl.

The term "alkynyl" refers to a straight or branched chain hydrocarbyl radical having at least one carbon-carbon triple bond, and having 2 to about 12 carbon atoms (with radicals having 2 to about 10 carbon atoms being preferred), e.g., ethynyl, propynyl, and butynyl.

The term "alkoxy" denotes an alkyl group attached via an oxygen linkage to the rest of the molecule. Representative examples of such groups are —$OCH_3$ and —$OC_2H_5$.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronapthtyl, adamantyl and norbornyl groups, bridged cyclic groups or sprirobicyclic groups, e.g., sprio(4,4)non-2-yl.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "cycloalkenyl" refers to a cyclic ring-containing radical having 3 to about 8 carbon atoms with at least one carbon-carbon double bond, such as cyclopropenyl, cyclobutenyl, and cyclopentenyl.

The term "aryl" refers to an aromatic radical having 6 to 14 carbon atoms such as phenyl, naphthyl, tetrahydronapthyl, indanyl, and biphenyl.

The term "arylalkyl" refers to an aryl group as defined above directly bonded to an alkyl group as defined above, e.g., —$CH_2C_6H_5$ and —$C_2H_4C_6H_5$.

The term "heterocyclyl" and "heterocyclic ring" "heterocyclic group" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuranyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heterocyclic ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

Unless otherwise specified, the term "substituted" as used herein refers to one or more of the substituents comprising of hydroxy, halogen, carboxyl, cyano, nitro, oxo (=O), thio (=S), substituted or unsubstituted alkyl, fully or partially substituted haloalkyl, substituted or unsubstituted alkoxy, fully or partially substituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(=N—$N(R^x)R^y$), —$NR^xC(O)OR^y$, —$NR^xR^y$, —$NR^xC(O)R^y$, —$NR^xC(S)R^y$, —$NR^xC(S)NR^yR^z$, —$SONR^xR^y$, —$SO_2NR^xR^y$, —$OR^x$, —$OR^xC(O)NR^yR^z$, —$OR^xC(O)OR^y$, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^y$, —$R^xOC(O)R^y$, —$SR^x$, —$SOR^x$, —$SO_2R^x$, and —$ONO_2$, wherein $R^x$, $R^y$ and $R^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "treating" or "treatment" of a state, disorder or condition includes:

(1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition;

(2) inhibiting the state, disorder or condition, i.e., arresting or reducing the development of the disease or at least one clinical or subclinical symptom thereof; or (3) relieving the disease, i.e., causing regression of the state, disorder or condition or at least one of its clinical or subclinical symptoms.

The benefit to a subject to be treated is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compound described in the present patent application may form salts. Non-limiting examples of pharmaceutically acceptable salts forming part of this patent application include salts derived from inorganic bases, salts of organic bases, salts of chiral bases, salts of natural amino acids and salts of non-natural amino acids. Certain compounds of present patent application are capable of existing in stereoisomeric forms (e.g. diastereomers and enantiomers).

With respect to the overall compounds described by the Formula (I), the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutical Compositions

The pharmaceutical composition provided in the present invention include at least one compound described herein and at least one pharmaceutically acceptable excipient (such as a pharmaceutically acceptable carrier or diluent). Preferably, the contemplated pharmaceutical compositions include the compound(s) described herein in an amount sufficient to inhibit TRPV3 receptor in a subject.

The subjects contemplated include, for example, a living cell and a mammal, including human mammal. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques, e.g., as described in Remington: The Science and Practice of Pharmacy, $20^{th}$ Ed., 2003 (Lippincott Williams & Wilkins). For example, the active compound can be mixed with a carrier, or diluted by a carrier, or enclosed within a carrier, which may be in the form of an ampoule, capsule, sachet, paper, or other container. When the carrier serves as a diluent, it may be a solid, semisolid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), 250 mg colloidal silicon dioxide (Aerosil®), 1.5 mg microcrystalline cellulose (Avicel®), 70 mg modified cellulose gum (Ac-Di-Sol®), and 7.5 mg magnesium stearate; (2) Coating: HPMC, approx. 9 mg Mywacett 9-40 T and approx. 0.9 mg acylated monoglyceride Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The present invention provides compounds and pharmaceutical formulations thereof that are useful in the treatment of diseases, conditions and/or disorders modulated by TRPV3. The connection between therapeutic effect and inhibition of TRPV3 is illustrated, for example in WO2007/056124; Wissenbach, U. et al, Biology of the cell (2004), 96, 47-54; Nilius, B. et al., Physiol Rev (2007), 87, 165-217; Okuhara, D. Y. et al, Expert Opinion on Therapeutic Targets (2007), 11, 391-401; Hu, H. Z. et al, Journal of Cellular Physiology, (2006), 208, 201-212 and references cited therein, all of which are incorporated herein by reference in their entirety and for the purpose stated The present patent application further provides a method of treating a disease, condition and/or disorder modulated by TRPV3 in a subject in need thereof by administering to the subject a therapeutically effective amount of a compound or a pharmaceutical composition of the present invention.

Diseases, conditions, and/or disorders that are modulated by TRPV3 are believed to include, but are not limited to, migraine, arthralgia, cardiac pain arising from an ischemic myocardium, acute pain, chronic pain, neuropathic pain, post-operative pain, pain due to neuralgia (e.g., post-herpetic neuralgia or trigeminal neuralgia), pain due to diabetic neuropathy, dental pain and cancer pain, inflammatory pain conditions (e.g. arthritis and osteoarthritis).

Also Diseases, conditions, and/or disorders that are modulated by TRPV3 are believed to include, but are not limited to pain, nociceptive pain, dental pain, cardiac pain arising from an ischemic myocardium, pain due to migraine, arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratocanthoma, alopecia, Meniere's disease, tinnitus, hyperacusis, anxiety disorders and benign prostate hyperplasia.

General Methods of Preparation

The compounds of the present invention, described herein, may be prepared by techniques known in the art. The pyrido[1,2-a]pyrimidine derivatives with appropriate substitution can be prepared according to a procedure described in (a) Hauser, C. R.; Weiss, M. J. J. Org. Chem. (1949), 14, 453-459; (b) Satti, N. K.; Suri, K. A.; Suri, O. P.; Kapil, A. Indian J. Chem. Sect. B, (1993), 32, 978-980. Condensation of 2-methyl-3-halopyrido[1,2-a]pyrimidines with aryl aldehydes can be accomplished according to a procedure described in Yale, Spitzmiller, et al. J. Heterocyclic Chem. (1976), 13, 869-871. The final compounds of the present invention can be prepared by a Suzuki coupling and useful coupling procedures for such reactions may be found in (a) Miyaura; Suzuki, A., Chem. Rev. (1995), 95, 2457-2483; (b) Huff, et al. Org. Synth. (1997), 75, 53-60. Specific methods adopted for the synthesis are depicted in Synthetic Schemes 1 and 2. The compounds of the present invention may be prepared by alternative approaches known in the art and such methods are included within the scope of the present invention.

The compound of the formula (I) where R, $R^1$, $R^2$, 'A', 'm' and 'n' are as described previously can be prepared from appropriately substituted 2-aminopyridines (1) as shown in synthetic Scheme 1. Thus, 2-aminopyridine (1) was condensed with a β-keto ester of the formula (2) (where R' is hydrogen or alkyl) in acetic acid at elevated temperature to give pyrido[1,2-a]pyrimidine derivative of the formula (3). Halogenation of compounds of formula (3) with a suitable halogenating agent such as bromine in acetic acid, n-bromosuccinimide or n-iodosuccinimide in an appropriate solvent gives compounds of formula (4) where X is halogen. Condensation of compounds of formula (4) with an aldehyde of the formula (5) in the presence of a suitable base such as sodium ethoxide, in a suitable solvent such as ethanol gives a compound formula (6). Palladium(0) assisted Suzuki coupling of (6) with an aryl and heteroaryl boronic acid of the formula (7) in the in the presence of a suitable base such as sodium carbonate in a suitable solvent gives compounds of the formula (I).

Synthetic Scheme 1

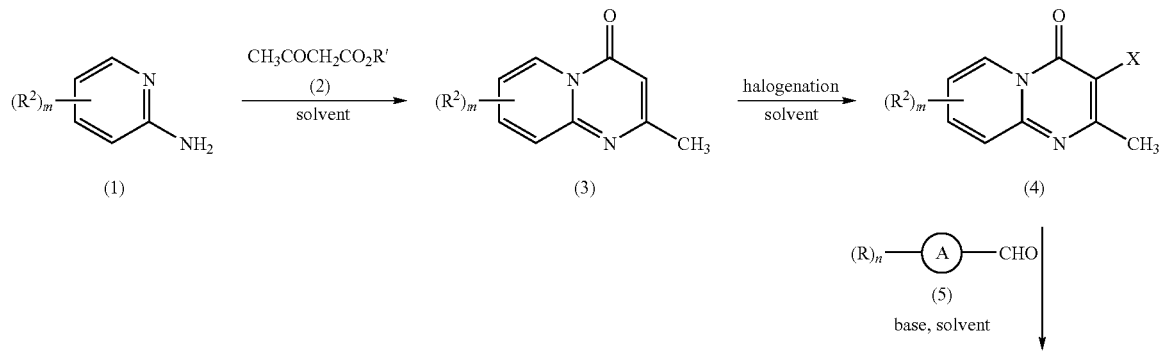

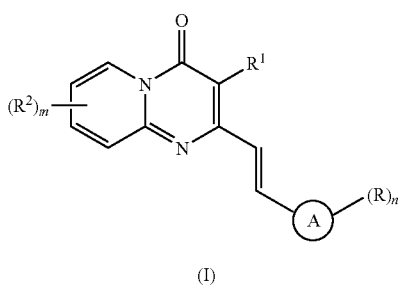
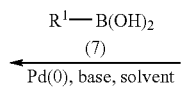
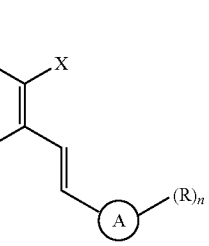

Alternatively, the compounds of the present invention (I) where R, $R^1$, $R^2$, 'A', 'm' and 'n' are as described previously may be prepared by sequence shown in Synthetic Scheme 2. The pyrido[1,2-a]pyrimidine derivative of the formula (3) prepared as described in Synthetic Scheme 1, is first condensed with an aldehyde of the formula (5) and subsequently halogenated with an appropriate halogenating agent as described above to give intermediate (6) where X is halogen. Intermediate (6) was converted to compounds of the general formula (I) by a Suzuki coupling with an appropriate aryl and heteroaryl boronic acid (7) as described previously.

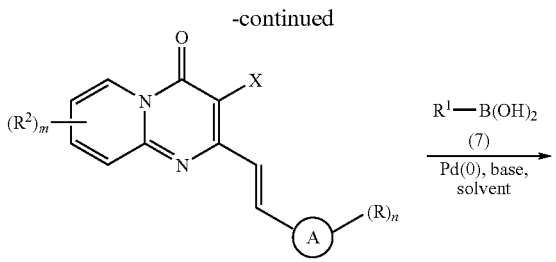

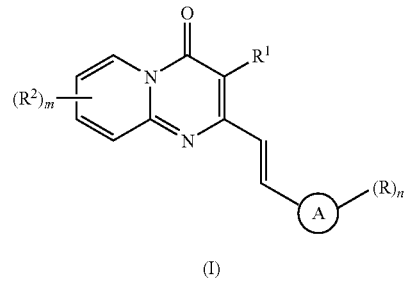

Specific examples represented by the formula (II) where R, $R^2$, Ar, 'm' and 'n' are as described previously were prepared as shown in Synthetic Scheme 3. Thus, 3-halo-2-methyl-4H-pyrido[1,2-a]pyrimidin-4-one (4) was reacted with 2,3-dialkoxybenzaldehyde of the formula (8) in the in the presence of a suitable base such as sodium ethoxide in protic solvent such as ethanol to give compounds of the formula (9). Intermediate (9) was converted to compounds of the general formula (II) by a Suzuki coupling with an appropriate aryl and heteroaryl boronic acid (7) as described previously. The compounds of the general formula (II) can also be prepared by condensation of 3-aryl-2-methyl-4H-pyrido[1,2-a]pyrimidin-4-one (10) with aryl aldehyde of the formula (8) using appropriate base in a suitable solvent.

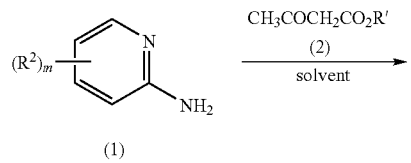

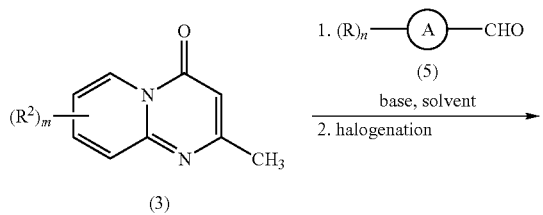

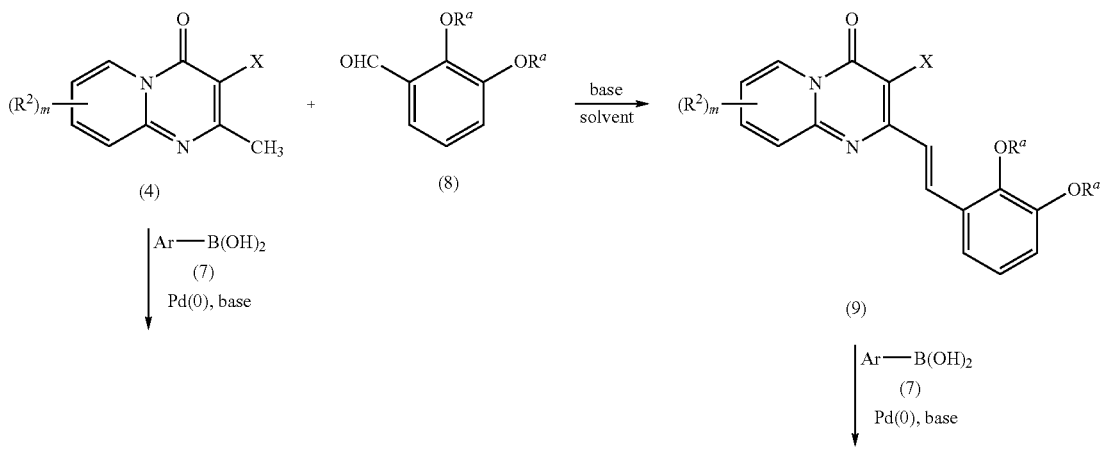

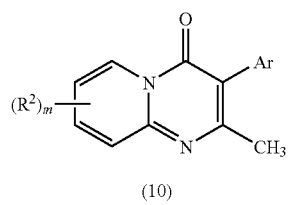 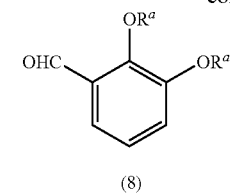 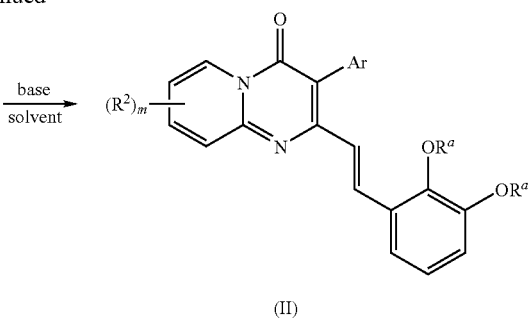

(10) (8) (II)

Intermediates

3-Bromo-2-methyl-4H-pyrido[1,2-a]pyrimidin-4-one derivatives

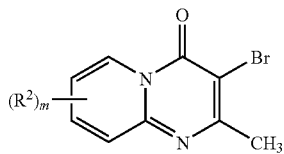

All the 3-bromo-2-methyl-4H-pyrido[1,2-a]pyrimidin-4-ones were prepared from commercially available 2-aminopyridine derivatives. Thus, 2-aminopyridine derivative was reacted with ethyl acetoacetate in refluxing acetic acid to give 2-methyl-4H-pyrido[1,2-a]pyrimidin-4-one in good yield. This intermediate was brominated using bromine in acetic acid to give 3-bromo-2-methyl-4H-pyrido[1,2-a]pyrimidin-4-ones in good yield. All the intermediates prepared in this manner were characterized by spectral and analytical methods before using them for the preparation of compounds of invention.

The aryl and heteroaryl aldehydes required for the synthesis were either commercially available or prepared from commercially available aldehydes. Most of the dialkoxy benzaldehydes were prepared by alkylation of 2-hydroxy-3-methoxybenzaldehyde (o-vanillin) with appropriate alkyl halide in the presence of potassium carbonate in N,N-dimethylformamide.

The following intermediates were prepared and used for the synthesis of compounds of present invention.

Intermediate 1

3-Bromo-2-{(E)-2-[4-chlorophenyl]vinyl}-4H-pyrido[1,2-a]pyrimidin-4-one

To a stirred solution of 3-bromo-2-methyl-4H-pyrido[1,2-a]pyrimidin-4-one (200 mg, 0.831 mmol) and sodium ethoxide (113 mg, 1.661 mmol) in absolute ethanol (20 ml) was added 4-chlorobenzaldehyde (176 mg, 1.257 mmol). The reaction mixture was heated to reflux for 6 h under nitrogen. The reaction mixture was cooled to room temperature. The residue obtained after evaporation was partitioned between chloroform (100 ml) and water (50 ml). The organic layer was washed with brine (50 ml), dried ($Na_2SO_4$) and concentrated to afford a crude product which was purified by silica gel column chromatography using 1% methanol in chloroform to give 275 mg of the product as a light yellow solid; IR (KBr) 3129, 2966, 2342, 1685, 1624, 1525, 1091, 821 $cm^{-1}$; $^1H$ NMR (300 MHz, $CDCl_3$) δ 7.09 (d, J=15.0 Hz, 1H), 7.37 (d, J=7.8 Hz, 4H), 7.50-7.70 (m, 3H), 7.99 (d, J=15.6 Hz, 1H), 8.97 (d, J=6.9 Hz, 1H).

Intermediate 2

3-Bromo-2-[(E)-2-pyridin-3-ylvinyl]-4H-pyrido[1,2-a]pyrimidin-4-one

The title compound was prepared from 3-bromo-2-methyl-4H-pyrido[1,2-a]pyrimidin-4-one (250 mg, 1.045 mmol) and pyridine-3-aldehyde (168 mg, 1.561 mmol) in the presence of sodium ethoxide (142 mg, 2.086 mmol) in absolute ethanol (25 ml) as described in Intermediate 1 to give 203 mg of the product as a light yellow solid; $^1H$ NMR (300 MHz, $CDCl_3$) δ 7.11 (t, J=6.9 Hz, 1H), 7.32-7.36 (m, 1H), 7.63-7.76 (m, 3H), 7.98-8.05 (m, 2H), 8.57 (d, J=4.8 Hz, 1H), 8.35 (s, 1H), 8.97 (d, J=6.6 Hz, 1H).

Intermediate 3

3-Bromo-2-[(E)-2-(2-thienyl)vinyl]-4H-pyrido[1,2-a]pyrimidin-4-one

The title compound was prepared from 3-bromo-2-methyl-4H-pyrido[1,2-a]pyrimidin-4-one (500 mg, 2.091 mmol) and thiophene-2-carboxaldehyde (351 mg, 3.129 mmol) in the presence of sodium ethoxide (284 mg, 4.175 mmol) in absolute ethanol (25 ml) as described in Intermediate 1 to give 283 mg of the product as a light yellow solid; $^1H$ NMR (300 MHz, $CDCl_3$) δ 7.06 (s, 2H), 7.31-7.43 (m, 3H), 7.63 (dd, J=2.4, 16.2 Hz, 2H), 8.15 (d, J=14.7 Hz, 1H), 8.94 (d, J=6.9 Hz, 1H).

Intermediate 4

2-[(E)-2-(1,3-Benzodioxol-4-yl)vinyl]-3-bromo-4H-pyrido[1,2-a]pyrimidin-4-one The title compound was prepared from 3-bromo-2-methyl-4H-pyrido[1,2-a]pyrimidin-4-one (1.5 g, 6.271 mmol) and 1,3-benzodioxole-4-carbaldehyde (1.12 g, 7.463 mmol) in the presence of sodium ethoxide (640 mg, 9.401 mmol) in absolute ethanol (100 ml) as described in Intermediate 1 to give 1.5 g of the product as a light yellow solid; $^1H$ NMR (300 MHz, $CDCl_3$) δ 4.48 (s, 2H), 6.83-6.89 (m, 2H), 7.05-7.10 (m, 2H), 7.19 (t, J=6.9 Hz, 1H), 7.69 (d, J=9.3 Hz, 1H), 7.78-7.85 (m, 1H), 7.97 (d, J=15.6 Hz, 1H), 8.94 (d, J=7.2 Hz, 1H).

Intermediate 5

3-Bromo-2-{(E)-2-[2-(cyclopentyloxy)-3-methoxyphenyl]vinyl}-4H-pyrido[1,2-a]-pyrimidin-4-one The title compound was prepared from 3-bromo-2-methyl-4H-pyrido[1,2-a]pyrimidin-4-one (500 mg, 2.091 mmol) and 2-(cyclopentyloxy)-3-methoxybenzaldehyde (514 mg, 2.503 mmol) in the presence of sodium ethoxide (213 mg, 3.131 mmol) in absolute ethanol (15 ml) as described in Intermediate 1 to give 383 mg of the product as a light yellow solid; $^1$H NMR (CDCl$_3$) δ 1.61-1.69 (m, 4H), 1.70-1.79 (m, 4H), 2.33 (s, 3H), 4.51 (br s, 1H), 7.01-7.07 (m, 2H), 7.12-7.24 (m, 1H), 7.57-7.60 (m, 4H), 8.43 (d, J=15.6 Hz, 1H), 8.94 (d, J=6.3 Hz, 1H).

Intermediate 6

3-Bromo-2-[(E)-2-(3-methoxy-2-propoxyphenyl)vinyl]-4H-pyrido[1,2-a]pyrimidin-4-one The title compound was prepared from 3-bromo-2-methyl-4H-pyrido[1,2-a]pyrimidin-4-one (1.2 g, 5.012 mmol) and (3-methoxy-2-propoxy)benzaldehyde (1.17 g, 6.021 mmol) in the presence of sodium ethoxide (0.512 g, 7.521 mmol) in absolute ethanol (25 ml) as described in Intermediate 1 to give 681 mg of the product as a light yellow solid; $^1$H NMR (300 MHz, CDCl$_3$) δ 1.15 (t, J=7.8 Hz, 3H), 1.89 (q, J=7.2 Hz, 2H), 3.87 (s, 3H), 3.99 (t, J=6.6 Hz, 2H), 6.91 (d, J=7.5 Hz, 1H), 7.05-7.11 (m, 2H), 7.33 (d, J=7.2 Hz, 1H), 7.58-7.70 (m, 3H), 8.42 (d, J=13.8 Hz, 1H), 8.94 (d, J=6.9 Hz, 1H).

Intermediate 7

3-Bromo-2-[(E)-2-(2-butoxy-3-methoxyphenyl)vinyl]-4H-pyrido[1,2-a]pyrimidin-4-one The title compound was prepared from 3-bromo-2-methyl-4H-pyrido[1,2-a]pyrimidin-4-one (1.30 g, 5.43 mmol) and (2-butoxy-3-methoxy)benzaldehyde (1.35 g, 6.481 mmol) in the presence of sodium ethoxide (0.55 g, 8.08 mmol) in absolute ethanol (25 ml) as described in Intermediate 1 to give 582 mg of the product as a light yellow solid; $^1$H NMR (300 MHz, CDCl$_3$) δ 1.01 (t, J=7.2 Hz, 3H), 1.59-1.65 (m, 2H), 1.85 (q, J=7.8 Hz, 2H) 3.87 (s, 3H), 4.02 (t, J=6.3 Hz, 2H), 6.91 (d, J=7.8 Hz, 1H), 7.04-7.10 (m, 2H), 7.33 (d, J=6.9 Hz, 1H), 7.58-7.70 (m, 3H), 8.41 (d, J=15.6 Hz, 1H), 8.95 (d, J=7.2 Hz, 1H).

Intermediate 8

3-Bromo-2-{(E)-2-[3-methoxy-2-(pentyloxy)phenyl]vinyl}-4H-pyrido[1,2-a]pyrimidin-4-one The title compound was prepared from 3-bromo-2-methyl-4H-pyrido[1,2-a]pyrimidin-4-one (1.20 g, 5.01 mmol) and 3-methoxy-2-(pentyloxy)benzaldehyde (1.22 g, 5.521 mmol) in the presence of sodium ethoxide (0.512 g, 7.52 mmol) in absolute ethanol (30 ml) as described in Intermediate 1 to give 625 mg of the product as a light yellow solid; $^1$H NMR (300 MHz, CDCl$_3$) δ 0.92 (t, J=6.9 Hz, 3H), 1.40 (q, J=7.2 Hz, 2H), 1.51-1.59 (m, 2H), 1.85 (q, J=7.8 Hz, 2H) 3.87 (s, 3H), 4.01 (t, J=6.3 Hz, 2H), 6.91 (d, J=7.8 Hz, 1H), 7.05-7.11 (m, 2H), 7.33 (d, J=7.8 Hz, 1H), 7.60-7.71 (m, 3H), 8.40 (d, J=15.9 Hz, 1H), 8.96 (d, J=6.6 Hz, 1H).

Intermediate 9

3-Bromo-2-{(E)-2-[2-(hexyloxy)-3-methoxyphenyl]vinyl}-4H-pyrido[1,2-a]pyrimidin-4-one The title compound was prepared from 3-bromo-2-methyl-4H-pyrido[1,2-a]pyrimidin-4-one (1.501 g, 6.271 mmol) and 3-methoxy-2-(hexyloxy)benzaldehyde (1.642 g, 6.942 mmol) in the presence of sodium ethoxide (0.642 g, 9.401 mmol) in absolute ethanol (30 ml) as described in Intermediate 1 to give 986 mg of the product as a light yellow solid; $^1$H NMR (300 MHz, CDCl$_3$) δ 0.84-0.90 (m, 3H), 1.30-1.38 (m, 4H), 1.52-1.58 (m, 2H), 1.88 (t, J=6.9 Hz, 2H) 3.87 (s, 3H), 4.01 (t, J=6.9 Hz, 2H), 6.90 (d, J=8.1 Hz, 1H), 7.04-7.10 (m, 2H), 7.31 (d, J=7.8 Hz, 1H), 7.59-7.70 (m, 3H), 8.38 (d, J=15.6 Hz, 1H), 8.94 (d, J=7.5 Hz, 1H).

Intermediate 10

3-Bromo-2-[(E)-2-{2-[2-(dimethylamino)ethoxy]-3-methoxyphenyl}vinyl]-4H-pyrido-[1,2-a]pyrimidin-4-one The title compound was prepared from 3-bromo-2-methyl-4H-pyrido[1,2-a]pyrimidin-4-one (1.021 g, 4.18 mmol) and 2-[2-(dimethylamino)ethoxy]-3-methoxybenzaldehyde (0.969 g, 5.011 mmol) in the presence of sodium ethoxide (0.426 g, 6.27 mmol) in absolute ethanol (25 ml) as described in Intermediate 1 to give 649 mg of the product as a light yellow solid; $^1$H NMR (300 MHz, CDCl$_3$) δ 2.39 (s, 6H), 2.82 (s, 2H), 3.87 (s, 3H), 4.12 (s, 2H), 6.91 (d, J=7.5 Hz, 1H), 7.04-7.10 (m, 2H), 7.28-7.34 (m, 1H), 7.66-7.71 (m, 3H), 8.40 (d, J=15.0 Hz, 1H), 8.95 (d, J=7.2 Hz, 1H).

Intermediate 11

3-Bromo-2-{(E)-2-[2-(cyclopropylmethoxy)-3-methoxyphenyl]vinyl}-4H-pyrido[1,2-a]pyrimidin-4-one The title compound was prepared from 3-bromo-2-methyl-4H-pyrido[1,2-a]pyrimidin-4-one (1.0 g, 4.181 mmol) and 2-(cyclopropylmethoxy)-3-methoxybenzaldehyde (1.29 g, 6.255 mmol) in the presence of sodium ethoxide (0.56 g, 8.361 mmol) in absolute ethanol (30 ml) as described in Intermediate 1 to give 424 mg of the product as a light yellow solid; $^1$H NMR (300 MHz, CDCl$_3$) δ 0.35-0.40 (m, 2H), 0.60-0.79 (m, 2H), 1.30-1.40 (m, 1H), 3.82-3.90 (m, 5H), 6.90 (d, J=7.8 Hz, 1H), 7.04-7.12 (m, 2H), 7.33 (d, J=7.8 Hz, 1H), 7.62-7.72 (m, 3H), 8.48 (d, J=15.6 Hz, 1H), 8.95 (d, J=7.5 Hz, 1H).

Intermediate 12

3-Bromo-2-{(E)-2-[2-(cyclopentyloxy)-3-methoxyphenyl]vinyl}-4H-pyrido[1,2-a]pyrimidin-4-one The title compound was prepared from 3-bromo-2-methyl-4H-pyrido[1,2-a]pyrimidin-4-one (700 mg, 2.921 mmol) and 2-(cyclopentyloxy)-3-methoxybenzaldehyde (998 mg, 4.391 mmol) in the presence of sodium ethoxide (398 mg, 5.842 mmol) in absolute ethanol (30 ml) as described in Intermediate 1 to give 358 mg of the product as a light yellow solid; IR (KBr) 2958, 1679, 1620, 1528, 1436, 1264, 1065, 971 cm$^{-1}$; $^1$H NMR (300 MHz, CDCl$_3$) δ 1.60-1.75 (m, 4H), 1.95-2.10 (m, 4H), 3.87 (s, 3H), 4.94 (br s, 1H), 6.90 (d, J=7.8 Hz, 1H), 7.02-7.10 (m, 1H), 7.35 (d, J=7.5 Hz, 2H), 7.56-7.72 (m, 3H), 8.44 (d, J=16.2 Hz, 1H), 8.94 (d, J=7.2 Hz, 1H).

Intermediate 13

3-Bromo-2-{(E)-2-[2-(cyclopentyloxy)-3-methoxyphenyl]vinyl}-9-methyl-4H-pyrido-[1,2-a]pyrimidin-4-one The title compound was prepared from 3-bromo-2,9-dimethyl-4H-pyrido[1,2-a]pyrimidin-4-one (1.5 g, 5.928 mmol) and (2-cyclopentyloxy-3-methoxy)benzaldehyde (1.95 g, 8.893 mmol) in the presence of sodium ethoxide (600 mg, 8.893 mmol) in absolute ethanol (40 ml) as described in Intermediate 1 to give 368 mg of the product as a light yellow solid; $^1$H NMR (300 MHz, CDCl$_3$) 1.60-1.70 (m, 4H), 1.82-1.95 (m, 4H), 2.66 (s, 3H), 3.86 (s, 3H), 4.90 (br s, 1H), 6.88-6.94 (m, 2H), 7.05 (t, J=7.8 Hz, 1H), 7.35 (d, J=8.4 Hz, 1H), 7.53 (d, J=6.0 Hz, 1H), 7.61 (d, J=15.6 Hz, 1H), 8.47 (d, J=15.6 Hz, 1H), 8.85 (d, J=6.6 Hz, 1H).

Intermediate 14

3-Bromo-2-{(E)-2-[2-(cyclopentyloxy)-3-methoxyphenyl]vinyl}-9-methoxy-4H-pyrido-[1,2-a]pyrimidin-4-one The title compound was prepared from 3-bromo-9-methoxy-2-methyl-4H-pyrido[1,2-a]pyrimidin-4-one (1.4 g, 5.202 mmol) and 2-(cyclopentyloxy-3-methoxy)benzaldehyde (1.37 g, 6.423 mmol) in the presence of sodium ethoxide (701 mg, 10.403 mmol) in absolute ethanol (50 ml) as described in Intermediate 1 to give 501 mg of the product as a light yellow solid; $^1$H NMR (300 MHz, CDCl$_3$) δ 1.63-1.73 (m, 4H), 2.00-2.07 (m, 4H), 3.86 (s, 3H), 4.03 (s, 3H), 4.94 (br s, 1H), 6.88-6.94 (m, 3H), 7.05 (t, J=7.8 Hz, 1H), 7.35 (d, J=8.4 Hz, 1H), 7.63 (d, J=15.6 Hz, 1H), 8.27 (d, J=15.6 Hz, 1H), 8.57 (d, J=6.6 Hz, 1H).

Intermediate 15

3-Bromo-7-chloro-2-{(E)-2-[2-(cyclopropylmethoxy)-3-methoxyphenyl]vinyl}-4H-pyrido[1,2-a]pyrimidin-4-one The title compound was prepared from 3-bromo-7-chloro-2-methyl-4H-pyrido[1,2-a]pyrimidin-4-one (1.17 g, 4.277 mmol) and (2-cyclopropyloxy-3-methoxy) benzaldehyde (1.06 mg, 5.132 mmol) in the presence of sodium ethoxide (582 mg, 8.554 mmol) in absolute ethanol (30 ml) as described in Intermediate 1 to give 369 mg of the product as a light yellow solid; $^1$H NMR (300 MHz, CDCl$_3$) δ 0.35-0.40 (m, 2H), 0.60-0.79 (m, 2H), 1.30-1.40 (m, 1H), 3.82 (d, J=6.6 Hz, 2H), 3.84 (s, 3H), 6.94 (d, J=7.8 Hz, 1H), 7.00-7.10 (m, 2H), 7.36 (d, J=7.8 Hz, 1H), 7.60-7.70 (m, 2H), 8.45 (d, J=15.6 Hz, 1H), 8.98 (d, J=7.5 Hz, 1H).

Intermediate 16

3-Bromo-7-chloro-2-{(E)-2-[2-(cyclopentyloxy)-3-methoxyphenyl]vinyl}-4H-pyrido-[1,2-a]pyrimidin-4-one The title compound was prepared from 3-bromo-7-chloro-2-methyl-4H-pyrido[1,2-a]pyrimidin-4-one (1 g, 3.656 mmol) and (2-cyclopentyloxy-3-methoxy)benzaldehyde (996 mg, 4.391 mmol) in the presence of sodium ethoxide (373 mg, 5.484 mmol) in absolute ethanol (30 ml) as described in Intermediate 1 to give 567 mg of the product as a light yellow solid; IR (KBr) 2962, 1682, 1531, 1262, 1068 cm$^{-1}$; $^1$H NMR (300 MHz, CDCl$_3$) δ 1.60-1.68 (m, 4H), 1.93-2.00 (m, 4H), 3.87 (s, 3H), 4.94 (br s, 1H), 6.90 (d, J=7.8 Hz, 1H), 7.06 (t, J=8.4 Hz, 1H), 7.34 (d, J=7.8 Hz, 1H), 7.50-7.61 (m, 3H), 8.43 (d, J=15.6 Hz, 1H), 8.94 (s, 1H).

Examples

The present invention is further illustrated by the following examples, which are not to be construed in any way as imposing limitations upon the scope of this disclosure, but rather are intended to be illustrative only.

General procedure for Suzuki coupling reaction: To a mixture of 3-bromo-2-(aryl)vinyl-4H-pyrido[1,2-a]pyrimidin-4-one intermediate (1.0 equivalent), arylboronic acid (1.0-1.2 equivalent) and Pd(PPh$_3$)$_4$ or PdCl$_2$(PPh$_3$)$_2$ (0.01 equivalent) in 50% aqueous methanol (10 ml) or 50% aqueous acetone (10 mug) was added sodium carbonate (2-3 equivalents) and mixture was refluxed under nitrogen until complete consumption of starting material is observed on TLC analysis (1-3 h). The reaction mixture was cooled to room temperature. Most of the organic solvent in the mixture was evaporated under reduced pressure and the residue obtained was diluted with chloroform (50 ml). The chloroform layer was washed with water (2×50 ml) followed by brine (50 ml). The organic layer was dried (Na$_2$SO$_4$) and concentrated to afford a crude product, which was purified by silica gel column chromatography using 2% acetone in chloroform or 10-20% EtOAc in n-hexane to give the title compounds.

Example 1

2-[(E)-2-(4-Chlorophenyl)vinyl]-3-phenyl-4H-pyrido[1,2-a]pyrimidin-4-one

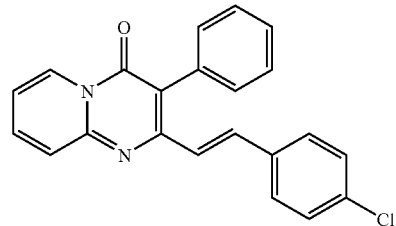 [SMILES: O=c1c(-c2ccccc2)c(/C=C/c2ccc(Cl)cc2)nc2ccccn12]

The title compound was prepared by Suzuki coupling reaction of Intermediate 1 (200 mg, 0.554 mmol) with phenylboronic acid (80 mg, 0.661 mmol) in the presence of Pd(PPh$_3$)$_4$ (38 mg, 0.054 mmol) and sodium carbonate (117 mg, 1.114 mmol) in aqueous acetone (3 ml) as described in general procedure to give 253 mg of the product as a light yellow solid; IR (KBr) 3056, 2361, 1661, 1625, 1523, 1091, 814 cm$^{-1}$; $^1$H NMR (300 MHz, CDCl$_3$) δ 6.98 (d, J=15.6 Hz, 1H), 7.24 (d, J=8.4 Hz, 4H), 7.33 (d, J=8.4 Hz, 2H), 7.40-7.50 (m, 4H), 7.60-7.70 (m, 2H), 7.91 (d, J=15.6 Hz, 1H), 8.98 (d, J=6.9 Hz, 1H); ESI-MS: m/z 359.32 [(M+H)$^+$, 100%], 361.20 (33%).

Example 2

2-{(E)-2-(Pyridin-3-yl)vinyl}-3-(4-trifluoromethyl)phenyl-4H-pyrido[1,2-a]pyrimidin-4-one

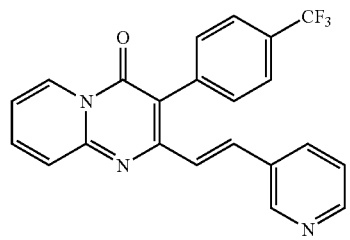 [SMILES: O=c1c(-c2ccc(C(F)(F)F)cc2)c(/C=C/c2cccnc2)nc2ccccn12]

The title compound was prepared by Suzuki coupling reaction of Intermediate 2 (150 mg, 0.457 mmol) with 4-trifluoromethylphenylboronic acid (104 mg, 0.547 mmol) in the presence of $PdCl_2(PPh_3)_2$ (52 mg, 0.045 mmol) and sodium carbonate (96 mg, 0.913 mmol) in aqueous methanol (5 ml) as described in general procedure to give 258 mg of the product as a light yellow solid; IR (KBr) 2925, 2359, 1670, 1626, 1517, 1325, 975 cm$^{-1}$; $^1$H NMR (CDCl$_3$) δ 7.00 (d, J=15.6 Hz, 1H), 7.11 (t, J=6.9 Hz, 1H), 7.25-7.35 (m, 1H), 7.56 (d, J=8.1 Hz, 2H), 7.70-7.80 (m, 5H), 8.02 (d, J=15.9 Hz, 1H), 8.50 (s, 1H), 8.68 (s, 1H), 9.00 (d, J=7.2 Hz, 1H); ESI-MS: m/z 394.30 (M+H)$^+$.

Example 3

2-[(E)-2-(2-Thienyl)vinyl]-3-[4-(trifluoromethyl)phenyl]-4H-pyrido[1,2-a]pyrimidin-4-one

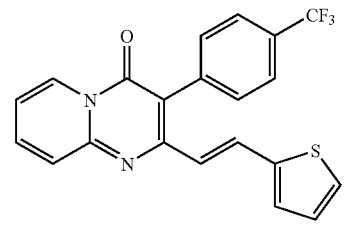 [SMILES: O=c1c(-c2ccc(C(F)(F)F)cc2)c(/C=C/c2cccs2)nc2ccccn12]

The title compound was prepared by Suzuki coupling reaction of intermediate 3 (180 mg, 0.540 mmol) with 4-trifluoromethylphenylboronic acid (123 mg, 0.647 mmol) in the presence of Pd(PPh$_3$)$_4$ (62 mg, 0.053 mmol) and sodium carbonate (114 mg, 1.072 mmol) in aqueous methanol (4 ml) as described in general procedure to give 254 mg of the product as a light yellow solid; IR (KBr) 2923, 2853, 2299, 1671, 1634, 1513, 1306, 961 cm$^{-1}$; $^1$H NMR (CDCl$_3$) δ 6.72 (d, J=15.0 Hz, 1H), 7.00-7.15 (m, 2H), 7.20-7.25 (m, 3H), 7.56 (d, J=7.8 Hz, 2H), 7.60-7.78 (m, 3H), 8.13 (d, J=15.3 Hz, 1H), 8.97 (d, J=6.9 Hz, 1H); ESI-MS: m/z 399.45 (M+H)$^+$.

Example 4

2-[(E)-2-(1,3-Benzodioxol-4-yl)vinyl]-3-[4-(trifluoromethyl)phenyl]-4H-pyrido[1,2-a]pyrimidin-4-one

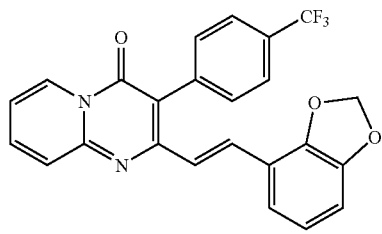 [SMILES: O=c1c(-c2ccc(C(F)(F)F)cc2)c(/C=C/c2cccc3c2OCO3)nc2ccccn12]

The title compound was prepared by Suzuki coupling reaction of Intermediate 4 (200 mg, 0.486 mmol) with 4-trifluoromethylphenylboronic acid (85 mg, 0.583 mmol) in the presence of $PdCl_2(PPh_3)_2$ (34 mg, 0.048 mmol) and sodium carbonate (103 mg, 0.972 mmol) in aqueous methanol (4 ml) as described in general procedure to give 261 mg of the product as a light yellow solid; IR (KBr) 3101, 2902, 1674, 1621, 1329, 1068 cm$^{-1}$; $^1$H NMR (CDCl$_3$) δ 5.90 (s, 2H), 6.72-6.80 (m, 2H), 6.87 (d, J=7.2 Hz, 1H), 7.03-7.09 (m, 1H), 7.15 (d, J=15.6 Hz, 1H), 7.57 (d, J=7.8 Hz, 2H), 7.68-7.72 (m, 4H), 7.94 (d, J=15.0 Hz, 1H), 8.98 (d, J=7.2 Hz, 1H); ESI-MS: m/z 437.52 (M+H)$^+$.

Example 5

4-{2-[(E)-2-[2-(Cyclopentyloxy)-3-methoxyphenyl]vinyl]-4-oxo-4H-pyrido[1,2-a]pyrimidin-3-yl}benzonitrile

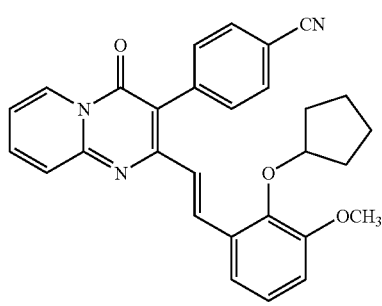

The title compound was prepared by Suzuki coupling reaction of Intermediate 5 (200 mg, 0.479 mmol) with 4-cyanophenylboronic acid (82 mg, 0.567 mmol) in the presence of PdCl$_2$(PPh$_3$)$_2$ (33 mg, 0.047 mmol) and sodium carbonate (99 mg, 0.948 mmol) in aqueous methanol (4 ml) as described in general procedure to give 201 mg of the product as a light yellow solid; $^1$H NMR (CDCl$_3$) δ 1.63-1.69 (m, 4H), 1.92-1.99 (m, 4H), 2.30 (s, 3H), 4.48 (br s, 1H), 6.85 (d, J=15.0 Hz, 1H), 6.92-6.98 (m, 1H), 7.07-7.14 (m, 4H), 7.57-7.60 (m, 3H), 7.63-7.74 (m, 2H), 8.44 (d, J=15.6 Hz, 1H), 8.96 (d, J=6.3 Hz, 1H).

Example 6

2-[(E)-2-[(3-Methoxy-2-propoxyphenyl)vinyl]-3-[4-(trifluoromethyl)phenyl]-4H-pyrido[1,2-a]pyrimidin-4-one

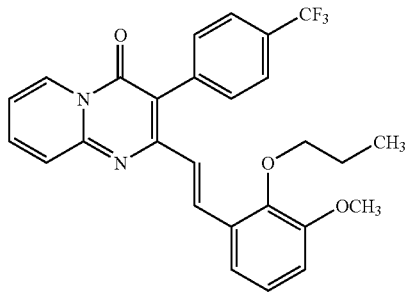

The title compound was prepared by Suzuki coupling reaction of Intermediate 6 (180 mg, 0.427 mmol), 4-trifluoromethylphenylboronic acid (98 mg, 0.515 mmol) Pd(PPh$_3$)$_4$ (30 mg, 0.042 mmol) and sodium carbonate (92 mg, 0.867 mmol) in aqueous methanol (5 ml) as described in the general procedure to give 335 mg of the product as a light yellow solid; IR (KBr) 2964, 1665, 1619, 1323, 1114, 1069, 755 cm$^{-1}$; $^1$H NMR (300 MHz, CDCl$_3$) δ 1.09 (t, J=6.6 Hz, 3H), 1.75 (q, J=6.9 Hz, 2H), 3.84 (s, 3H), 3.91 (t, J=6.6 Hz, 2H), 6.82-6.89 (m, 1H), 6.97-7.06 (m, 4H), 7.56 (d, J=8.1 Hz, 2H), 7.62-7.72 (m, 4H), 8.38 (d, J=15.6 Hz, 1H), 8.97 (d, J=7.5 Hz, 1H); APCI-MS: m/z 481.20 (M+H)$^+$.

Example 7

4-{2-[(E)-2-[(3-Methoxy-2-propoxyphenyl)vinyl]-4-oxo-4H-pyrido[1,2-a]pyrimidin-3-yl}benzonitrile

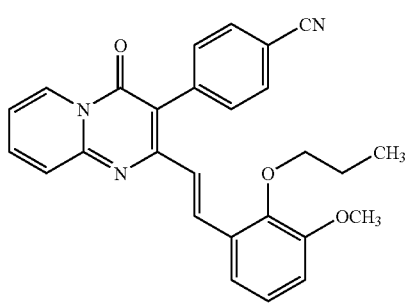 [SMILES: CCCOc1c(/C=C/c2nc3ccccn3c(=O)c2-c2ccc(C#N)cc2)cccc1OC]

The title compound was prepared by Suzuki coupling reaction of Intermediate 6 (180 mg, 0.433 mmol) with 4-cyanophenylboronic acid (76 mg, 0.519 mmol) in the presence of Pd(PPh$_3$)$_4$ (30 mg, 0.043 mmol) and sodium carbonate (92 mg, 0.867 mmol) in aqueous methanol (30 ml) as described in general procedure to give 218 mg of the product as a light yellow solid; IR (KBr) 2961, 1671, 1624, 1525, 1272, 1064 cm$^{-1}$; $^1$H NMR (300 MHz, CDCl$_3$) δ 1.10 (t, J=7.5 Hz, 3H), 1.77 (q, J=6.3 Hz, 2H), 3.84 (s, 3H), 3.92 (t, J=6.3 Hz, 2H), 6.85-6.90 (m, 1H), 6.97-7.08 (m, 4H), 7.57-7.63 (m, 3H), 7.70-7.80 (m, 3H), 8.40 (d, J=15.6 Hz, 1H), 8.97 (d, J=6.9 Hz, 1H); APCI-MS: m/z 438.25 (M+H)$^+$.

Example 8

2-[(E)-2-[(2-Butoxy-3-methoxyphenyl)vinyl]-3-[4-(trifluoromethyl)phenyl]-4H-pyrido-[1,2-a]pyrimidin-4-one

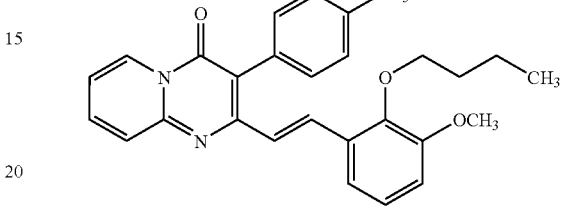

The title compound was prepared by Suzuki coupling reaction of Intermediate 7 (180 mg, 0.419 mmol) with 4-trifluoromethylphenylboronic acid (95 mg, 0.503 mmol) in the presence of PdCl$_2$(PPh$_3$)$_2$ (29 mg, 0.042 mmol) and sodium carbonate (88 mg, 0.838 mmol) in aqueous methanol (4 ml) as described in general procedure to give 261 mg of the product as a light yellow solid; IR (KBr) 2959, 1669, 1625, 1458, 1323, 1124, 1065 cm$^{-1}$; $^1$H NMR (300 MHz, CDCl$_3$) δ 0.99 (t, J=6.9 Hz, 3H), 1.68-1.75 (m, 4H), 3.83 (s, 3H), 3.95 (d, J=6.3 Hz, 2H), 6.82-6.89 (m, 1H), 6.97-7.06 (m, 4H), 7.56 (d, J=8.1 Hz, 2H), 7.65-7.72 (m, 4H), 8.36 (d, J=15.6 Hz, 1H), 8.97 (d, J=6.6 Hz, 1H). APCI-MS: m/z 495.67 (M+H)$^+$.

Example 9

2-[(E)-2-[2-Butoxy-3-methoxyphenyl)vinyl]-3-[4-(trifluoromethoxy)phenyl]-4H-pyrido-[1,2-a]pyrimidin-4-one

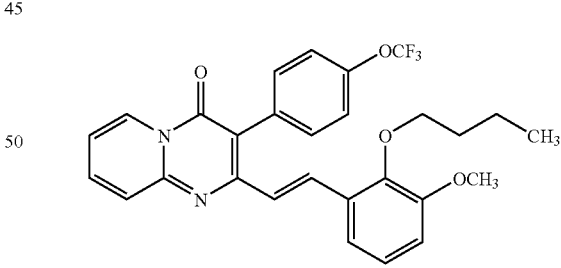

The title compound was prepared by Suzuki coupling reaction of Intermediate 7 (130 mg, 0.302 mmol) with 4-trifluoromethoxyphenylboronic acid (74 mg, 0.363 mmol) in the presence of PdCl$_2$(PPh$_3$)$_2$ (21 mg, 0.030 mmol) and sodium carbonate (88 mg, 0.838 mmol) in aqueous methanol (5 ml) as described in general procedure to give 301 mg of the product as a light yellow solid; IR (KBr) 2958, 1662, 1620, 1511, 1259, 1069, 769 cm$^{-1}$; $^1$H NMR (300 MHz, CDCl$_3$) δ 0.99 (d, J=7.2 Hz, 3H), 1.55-1.62 (m, 2H), 1.70-1.77 (m, 2H), 3.84 (s, 3H), 3.96 (t, J=6.3 Hz, 2H), 6.82-6.88 (m, 1H), 6.96-7.07 (m, 4H), 7.29 (d, J=7.8 Hz, 2H), 7.47 (d, J=8.4 Hz, 2H), 7.61-7.67

(m, 2H), 8.35 (d, J=15.6 Hz, 1H), 8.96 (d, J=6.9 Hz, 1H); APCI-MS: m/z 511.34 (M+H)+.

Example 10

4-{2-[(E)-2-[(2-Butoxy-3-methoxyphenyl)vinyl]-4-oxo-4H-pyrido[1,2-a]pyrimidin-3-yl}benzonitrile

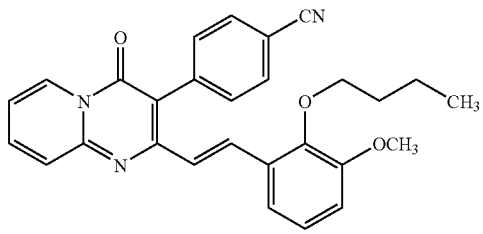 [SMILES: CCCCOc1c(/C=C/c2nc3ccccn3c(=O)c2-c2ccc(C(F)(F)F)cc2)cccc1OC]

The title compound was prepared by Suzuki coupling reaction of Intermediate 7 (180 mg, 0.419 mmol) with 4-cyanophenylboronic acid (73 mg, 0.503 mmol) in the presence of PdCl$_2$(PPh$_3$)$_2$ (29 mg, 0.042 mmol) and sodium carbonate (88 mg, 0.838 mmol) in aqueous methanol (4 ml) as described in general procedure to give 216 mg of the product as a light yellow solid; IR (KBr) 2959, 1664, 1615, 1523, 1269, 1068 cm$^{-1}$; $^1$H NMR (300 MHz, CDCl$_3$) δ 1.00 (t, J=6.9 Hz, 3H), 1.58-1.65 (m, 2H), 1.70-1.76 (m, 2H), 3.84 (s, 3H), 3.96 (t, J=6.9 Hz, 2H), 6.82-6.90 (m, 1H), 6.97-7.07 (m, 4H), 7.58 (d, J=7.8 Hz, 3H), 7.66-7.76 (m, 3H), 8.38 (d, J=15.6 Hz, 1H), 8.98 (d, J=6.3 Hz, 1H); APCI-MS: m/z 452.23 (M+H)+.

Example 11

2-[(E)-2-[(3-Methoxy-2-pentyloxyphenyl)vinyl]-3-[4-(trifluoromethyl)phenyl]-4H-pyrido[1,2-a]pyrimidin-4-one

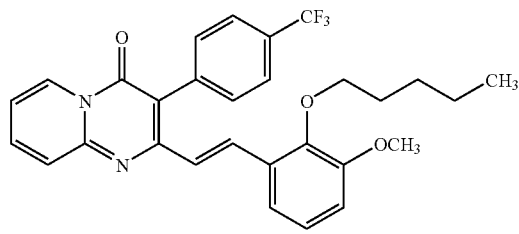 [SMILES: CCCCCOc1c(/C=C/c2nc3ccccn3c(=O)c2-c2ccc(C#N)cc2)cccc1OC]

The title compound was prepared by Suzuki coupling reaction of Intermediate 8 (181 mg, 0.406 mmol) with 4-trifluoromethylphenylboronic acid (92 mg, 0.487 mmol) in the presence of PdCl$_2$(PPh$_3$)$_2$ (28 mg, 0.040 mmol) and sodium carbonate (86 mg, 0.812 mmol) in aqueous methanol (4 ml) as described in general procedure to give 264 mg of the product as a light yellow solid; $^1$H NMR (300 MHz, CDCl$_3$) δ 0.93 (t, J=7.2 Hz, 3H), 1.35-1.42 (m, 2H), 1.46-1.58 (m, 2H), 1.69-1.76 (m, 3H), 3.84 (s, 3H), 3.95 (t, J=6.3 Hz, 2H), 6.85 (d, J=4.8 Hz, 1H), 6.97-7.06 (m, 3H), 7.08 (s, 1H), 7.57 (d, J=7.8

Hz, 1H), 7.70 (t, J=6.3 Hz, 4H), 8.37 (d, J=15.6 Hz, 1H), 8.98 (d, J=7.2 Hz, 1H); ESI-MS (m/z) 508.20 (M)+

Example 12

4-{2-[(E)-2-[3-Methoxy-2-pentyloxyphenyl)vinyl]-4-oxo-4H-pyrido[1,2-a]pyrimidin-3-yl}benzonitrile

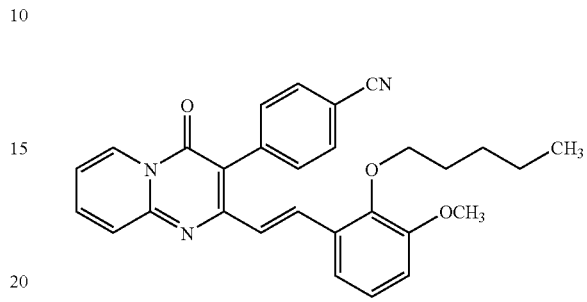

The title compound was prepared by Suzuki coupling reaction of Intermediate 8 (181 mg, 0.406 mmol) with 4-cyanophenylboronic acid (71 mg, 0.487 mmol) in the presence of PdCl$_2$(PPh$_3$)$_2$ (28 mg, 0.040 mmol) and sodium carbonate (86 mg, 0.812 mmol) in aqueous methanol (4 ml) as described in general procedure to give 302 mg of the product as a light yellow solid; $^1$H NMR (300 MHz, CDCl$_3$) δ 0.941 (t, J=7.5 Hz, 3H), 1.36-1.53 (m, 4H), 1.74 (t, J=6.0 Hz, 2H), 3.84 (s, 3H), 3.95 (t, J=6.3 Hz, 2H), 6.83-6.89 (m, 1H), 6.96-7.01 (m, 3H), 7.08 (t, J=6.0 Hz, 1H), 7.58 (d, J=8.4 Hz, 2H), 7.65-7.76 (m, 4H), 8.37 (d, J=15.6 Hz, 1H) 8.98 (d, J=7.2 Hz, 1H); ESI-MS: m/z 466.57 (M+H)+.

Example 13

2-[(E)-2-[(2-Hexyloxy-3-methoxyphenyl)vinyl]-3-[4-(trifluoromethyl)phenyl]-4H-pyrido[1,2-a]pyrimidin-4-one

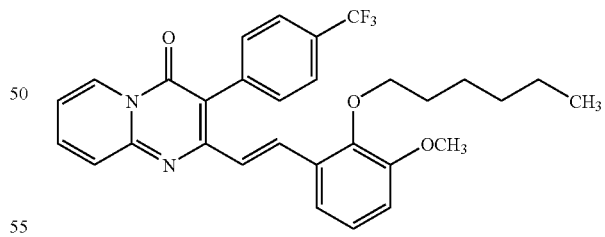

The title compound was prepared by Suzuki coupling reaction of Intermediate 9 (200 mg, 0.437 mmol) with 4-trifluoromethylphenylboronic acid (99 mg, 0.521 mmol) in the presence of PdCl$_2$(PPh$_3$)$_2$ (30 mg, 0.043 mmol) and sodium carbonate (92 mg, 0.845 mmol) in aqueous methanol (5 ml) as described in general procedure to give 262 mg of the product as a light yellow solid; $^1$H NMR (300 MHz, CDCl$_3$) δ 0.85 (m, 3H), 1.30-1.36 (m, 4H), 1.48-1.54 (m, 2H), 1.70-1.76 (m, 3H), 3.83 (s, 3H), 3.94 (t, J=6.3 Hz, 2H), 6.85 (d, J=4.2 Hz, 1H), 6.97-7.08 (m, 4H), 7.56 (d, J=7.8 Hz, 1H), 7.70 (t, J=10.8 Hz 4H), 8.36 (d, J=15.9 Hz, 1H) 8.97 (d, J=6.9 Hz, 1H); ESI-MS: m/z 523.25 (M+H)⁺.

Example 14

4-{2-[(E)-2-[(2-Hexyloxy-3-methoxyphenyl)vinyl]-4-oxo-4H-pyrido[1,2-a]pyrimidin-3-yl}benzonitrile

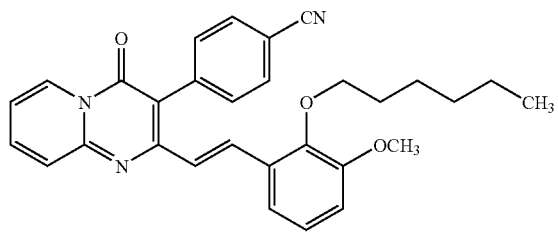 [SMILES: CCCCCCOc1c(/C=C/c2nc3ccccn3c(=O)c2-c2ccc(C#N)cc2)cccc1OC]

The title compound was prepared by Suzuki coupling reaction of Intermediate 9 (200 mg, 0.437 mmol) with 4-cyanophenyboronic acid (77 mg, 0.487 mmol) in the presence of PdCl₂(PPh₃)₂ (28 mg, 0.406 mmol) and sodium carbonate (86 mg, 0.812 mmol) in aqueous methanol (30 ml) as described in general procedure to give 277 mg of the product as a light yellow solid; ¹H NMR (300 MHz, CDCl₃) δ 0.85-0.92 (m, 3H), 1.30-1.37 (m, 4H), 1.48-1.53 (m, 2H), 1.70-1.76 (m, 2H), 3.84 (s, 3H), 3.95 (t, J=6.3 Hz, 2H), 6.82-6.90 (m, 1H), 6.95-7.01 (m, 2H), 7.08 (t, J=6.0 Hz, 1H), 7.35-7.41 (m, 1H), 7.58 (d, J=8.1 Hz, 2H), 7.64-7.76 (m, 4H), 8.36 (d, J=15.6 Hz, 1H), 8.97 (d, J=7.2 Hz, 1H); ESI-MS: m/z 479.22 (M)⁺.

Example 15

2-[(E)-2-{2-[2-(Dimethylamino)ethoxy]-3-methoxyphenyl}vinyl]-3-(4-trifluoromethyl phenyl)-4H-pyrido[1,2-a]pyrimidin-4-one hydrochloride

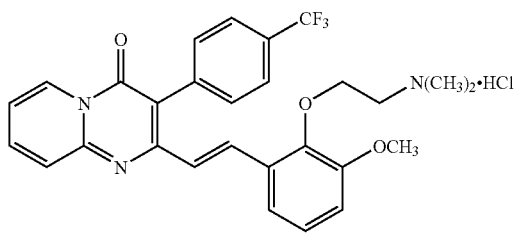

Step 1: 2-[(E)-2-{2-[2-(Dimethylamino)ethoxy]-3-methoxyphenyl}vinyl]-3-(4-trifluoro-methylphenyl)-4H-pyrido[1,2-a]pyrimidin-4-one: The title compound was prepared by Suzuki coupling reaction of Intermediate 10 (200 mg, 0.451 mmol) with 4-trifluoromethylphenylboronic acid (111 mg, 0.589 mmol) in the presence of PdCl₂(PPh₃)₂ (31 mg, 0.045 mmol) and sodium carbonate (95 mg, 0.902 mmol) in aqueous methanol (6 ml) as described in general procedure to give 279 mg of the product as a light yellow solid.

Step 2: 2-[(E)-2-{2-[2-(Dimethylamino)ethoxy]-3-methoxyphenyl}vinyl]-3-(4-trifluoro-methylphenyl)-4H-pyrido[1,2-a]pyrimidin-4-one hydrochloride: To a stirred solution of above compound (250 mg, 0.544 mmol) in ethyl acetate (2 ml) was added saturated solution of hydrochloric acid in ethyl acetate (3 ml) at 0° C. The reaction mixture was stirred at 0° C.-10° C. for 1 h. The solid separated out was collected by filtration and dried under reduced pressure to give 201 mg of the product as light yellow solid; IR (KBr) 3009, 2835, 1693, 1621, 1327, 1124, 1067 cm⁻¹; ¹H NMR (300 MHz, CDCl₃) δ 2.93 (s, 6H), 3.45 (s, 2H), 3.79 (s, 3H), 4.21 (s, 2H), 6.89 (d, J=16.2 Hz, 1H), 7.01 (s, 1H), 7.09 (s, 2H), 7.32-7.38 (m, 1H), 7.62-7.68 (m, 2H), 7.82-7.88 (m, 3H), 8.00-8.06 (m, 1H), 8.27 (d, J=16.2 Hz, 1H), 8.90-8.96 (m, 1H); APCI-MS: m/z 510.12 (M+H)⁺.

Example 16

2-{(E)-2-[2-(Cyclopropylmethoxy)-3-methoxyphenyl]vinyl}-3-phenyl-4H-pyrido[1,2-a]-pyrimidin-4-one

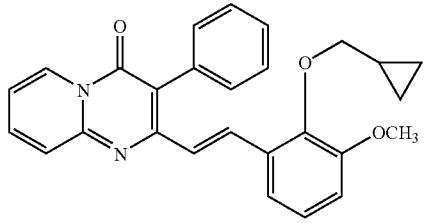 [SMILES: COc1cccc(/C=C/c2nc3ccccn3c(=O)c2-c2ccccc2)c1OCC1CC1]

The title compound was prepared by Suzuki coupling reaction of Intermediate 11 (50 mg, 0.117 mmol) with phenylboronic acid (17 mg, 0.140 mmol) in the presence of PdCl₂(PPh₃)₂ (13 mg, 0.011 mmol) and sodium carbonate (25 mg, 0.233 mmol) in aqueous methanol (4 ml) as described in general procedure to give 203 mg of the product as a light yellow solid; ¹H NMR (300 MHz, CDCl₃) δ 0.34-0.38 (m, 2H), 0.58-0.67 (m, 2H), 1.24 (br s, 1H), 3.79 (d, J=7.5 Hz, 1H), 3.83 (s, 3H), 6.81 (d, J=7.5 Hz, 1H), 6.90-7.10 (m, 4H), 7.30-7.40 (m, 5H), 7.64 (s, 2H), 8.40 (d, J=15.6 Hz, 1H), 8.97 (d, J=6.9 Hz, 1H); APCI-MS: m/z 425.35 (M+H)⁺.

Example 17

2-[(E)-2-[(2-Cyclopropylmethoxy-3-methoxyphenyl)vinyl]-3-[4-(trifluoromethyl)phenyl]-4H-pyrido[1,2-a]pyrimidin-4-one

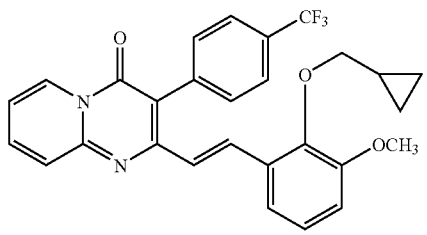 [SMILES: COc1cccc(/C=C/c2nc3ccccn3c(=O)c2-c2ccc(C(F)(F)F)cc2)c1OCC1CC1]

The title compound was prepared by Suzuki coupling reaction of Intermediate 11 (200 mg, 0.468 mmol) with 4-trifluoromethylphenylboronic acid (115 mg, 0.608 mmol) in the presence of PdCl₂(PPh₃)₂ (32 mg, 0.047 mmol) and sodium carbonate (99 mg, 0.936 mmol) in aqueous methanol (5 ml) as described general procedure to give 241 mg of the product as a light yellow solid; IR (KBr) 2944, 1663, 1619, 1322, 1115, 772 cm⁻¹; ¹H NMR (300 MHz, DMSO-d₆) δ 0.27-0.33 (m, 2H), 0.52 (d, J=7.2 Hz, 2H), 1.02-1.08 (m, 1H), 3.69 (d, J=7.2

Hz, 2H), 3.77 (s, 3H), 6.94 (d, J=15.6 Hz, 1H), 7.24-7.31 (m, 1H), 7.62-7.70 (m, 6H), 7.83 (d, J=7.8 Hz, 2H), 7.90-7.96 (m, 1H), 8.33 (d, J=15.6 Hz, 1H), 8.88 (d, J=7.8 Hz, 1H); APCI-MS: m/z 493.19 (M+H)+.

Example 18

2-[(E)-2-[(2-Cyclopropylmethoxy-3-methoxyphenyl) vinyl]-3-[4-(trifluoro-methoxy)phenyl]-4H-pyrido[1,2-a]pyrimidin-4-one

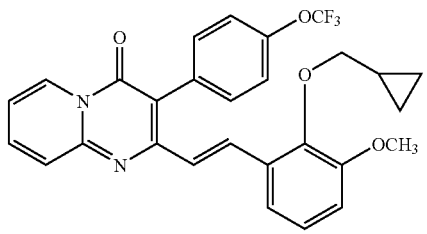 [SMILES: COc1cccc(/C=C/c2nc3ccccn3c(=O)c2-c2ccc(OC(F)(F)F)cc2)c1OCC1CC1]

The title compound was prepared by Suzuki coupling reaction of Intermediate 11 (150 mg, 0.351 mmol) with 4-trifluoromethoxyphenylboronic acid (86 mg, 0.421 mmol) in the presence of PdCl$_2$(PPh$_3$)$_2$ (24 mg, 0.035 mmol) and sodium carbonate (74 mg, 0.702 mmol) in aqueous methanol (5 ml) as described in general procedure to give 305 mg of the product as a light yellow solid; IR (KBr) 2945, 1663, 1620, 1530, 1264, 1205, 1172, 981 cm$^{-1}$; $^1$H NMR (300 MHz, DMSO-d$_6$) δ 0.36 (d, J=4.8 Hz, 2H), 0.60 (d, J=7.8 Hz, 2H), 1.20-1.28 (m, 1H), 3.78-3.86 (m, 5H), 6.80-6.86 (m, 1H), 6.98 (d, J=5.4 Hz, 2H), 7.03-7.10 (m, 2H), 7.30 (d, J=8.4 Hz, 2H), 7.47 (d, J=8.4 Hz, 2H), 7.63-7.69 (m, 2H), 8.43 (d, J=15.6 Hz, 1H), 8.97 (d, J=6.9 Hz, 1H); APCI-MS: m/z 509.20 (M+H)+.

Example 19

4-{2-[(E)-2[(2-Cyclopropylmethoxy-3-methoxyphenyl)vinyl]-4-oxo-4H-pyrido[1,2-a]pyrimidin-3-yl}benzonitrile

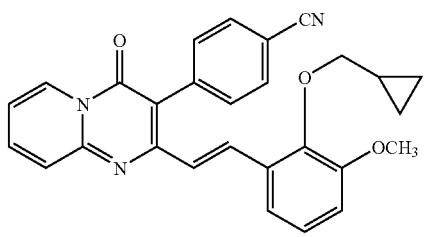 [SMILES: COc1cccc(/C=C/c2nc3ccccn3c(=O)c2-c2ccc(C#N)cc2)c1OCC1CC1]

The title compound was prepared by Suzuki coupling reaction of Intermediate 11 (200 mg, 0.468 mmol) with 4-cyanophenylboronic acid (90 mg, 0.608 mmol) in the presence of PdCl$_2$(PPh$_3$)$_2$ (32 mg, 0.046 mmol) and sodium carbonate (99 mg, 0.936 mmol) in aqueous methanol (5 ml) as described in general procedure to give 223 mg of the product as a light yellow solid; IR (KBr) 2916, 2231, 1666, 1524, 1270, 996 cm$^{-1}$; $^1$H NMR (300 MHz, DMSO-d$_6$) δ 0.26-0.34 (m, 2H), 0.54-0.60 (m, 2H), 1.05-1.12 (m, 1H), 3.70-3.80 (m, 5H), 6.89.7.00 (m, 4H), 7.27-7.33 (m, 1H), 7.60-7.70 (m, 3H), 7.90-7.98 (m, 3H), 8.33 (d, J=13.5 Hz, 1H), 8.85-8.91 (m, 1H); APCI-MS: m/z 450.24 (M+H)+.

Example 20

2-{(E)-2-[2-(Cyclopentyloxy)-3-methoxyphenyl] vinyl}-3-phenyl-4H-pyrido[1,2-a]-pyrimidin-4-one

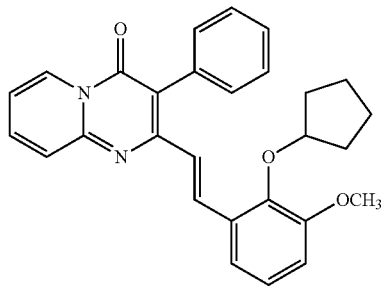 [SMILES: COc1cccc(/C=C/c2nc3ccccn3c(=O)c2-c2ccccc2)c1OC1CCCC1]

The title compound was prepared by Suzuki coupling reaction of Intermediate 12 (150 mg, 0.341 mmol) with phenylboronic acid (49 mg, 0.401 mmol) in the presence of PdCl$_2$(PPh$_3$)$_2$ (23 mg, 0.034 mmol) and sodium carbonate (72 mg, 0.679 mmol) in aqueous acetone (5 ml) as described in general procedure to give 232 mg of the product as a light yellow solid; IR (KBr) 2955, 1670, 1635, 1526, 1454, 1267, 1064, 759 cm$^{-1}$; $^1$H NMR (300 MHz, CDCl$_3$) δ 1.50-1.70 (m, 4H), 1.85-2.10 (m, 4H), 3.83 (s, 3H), 4.88 (br s, 1H), 6.81 (d, J=7.2 Hz, 1H), 6.90-7.10 (m, 4H), 7.30-7.50 (m, 5H), 7.60-7.70 (m, 2H), 8.38 (d, J=15.6 Hz, 1H), 8.96 (d, J=7.8 Hz, 1H); ESI-MS: m/z 439.22 (M+H)+.

Example 21

2-{(E)-2-[2-(Cyclopentyloxy-3-methoxy)phenyl] vinyl}-3-(3,5-difluoro) phenyl-4H-pyrido[1,2-a]pyrimidin-4-one

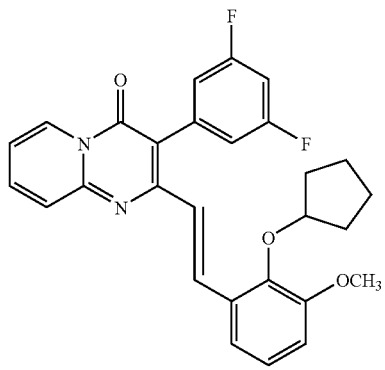 [SMILES: COc1cccc(/C=C/c2nc3ccccn3c(=O)c2-c2cc(F)cc(F)c2)c1OC1CCCC1]

The title compound was prepared by Suzuki coupling reaction of Intermediate 12 (150 mg, 0.341 mmol) with 3,5-difluorophenylboronic acid (64 mg, 0.408 mmol) in the presence of PdCl$_2$(PPh$_3$)$_2$ (23 mg, 0.034 mmol) and sodium carbonate (72 mg, 0.679 mmol) in aqueous methanol (5 ml) as described in general procedure to give 255 mg of the product as a light yellow solid; IR (KBr) 3084, 2959, 1667, 1628, 1527, 1262, 1087 cm$^{-1}$; $^1$H NMR (CDCl$_3$) δ 1.63-1.70 (m, 4H), 1.90-2.01 (m, 4H), 3.84 (s, 3H), 4.90 (br s, 1H), 6.85 (d, J=6.9 Hz, 2H), 6.93-7.05 (m, 5H), 7.13 (s, 1H), 7.59-7.72 (m, 2H), 8.42 (d, J=15.6 Hz, 1H), 8.95 (d, J=6.9 Hz, 1H); ESI-MS: m/z 475.31 (M+H)⁺.

Example 22

2-{(E)-2-[(2-Cyclopentyloxy-3-methoxy)phenyl]vinyl}-3-(3-trifluoromethyl)phenyl-4H-pyrido[1,2-a]pyrimidin-4-one

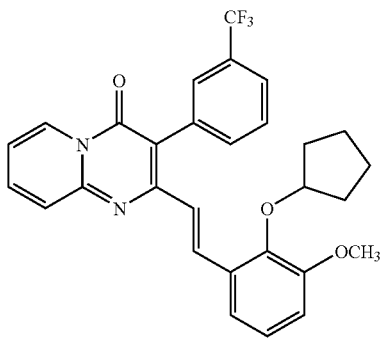 [SMILES: COc1cccc(/C=C/c2nc3ccccn3c(=O)c2-c2cccc(C(F)(F)F)c2)c1OC1CCCC1]

The title compound was prepared by Suzuki coupling reaction of Intermediate 12 (150 mg, 0.341 mmol) with 3-trifluoromethylphenylboronic acid (77 mg, 0.408 mmol) in the presence of PdCl$_2$(PPh$_3$)$_2$ (23 mg, 0.034 mmol) and sodium carbonate (72 mg, 0.679 mmol) in aqueous acetone (5 ml) as described in general procedure to give 281 mg of the product as a light yellow solid; IR (KBr) 2956, 1661, 1524, 1270, 1070 cm⁻¹; ¹H NMR (CDCl$_3$) δ 1.60-1.70 (m, 4H), 1.80-1.90 (m, 2H), 1.94-2.05 (m, 2H), 3.84 (s, 3H), 4.89 (br s, 1H), 6.83 (d, J=6.9 Hz, 1H), 6.88-7.00 (m, 4H), 7.05 (t, J=6.3 Hz, 1H), 7.52-7.74 (m, 5H), 8.42 (d, J=15.6 Hz, 1H), 8.96 (d, J=6.9 Hz, 1H); ESI-MS: m/z 507.36 (M+H)⁺.

Example 23

2-{(E)-2-[2-(Cyclopentyloxy)-3-methoxyphenyl]vinyl}-3-(4-trifluoromethyl)phenyl-4H-pyrido[1,2-a]pyrimidin-4-one

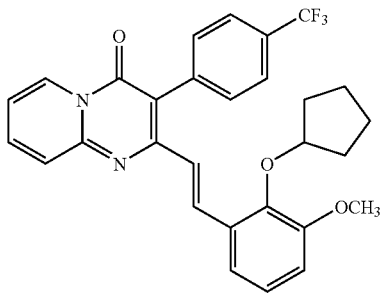 [SMILES: COc1cccc(/C=C/c2nc3ccccn3c(=O)c2-c2ccc(C(F)(F)F)cc2)c1OC1CCCC1]

The title compound was prepared by Suzuki coupling reaction of Intermediate 12 (200 mg, 0.453 mmol) with 4-trifluoromethylphenylboronic acid (103 mg, 0.542 mmol) in the presence of PdCl$_2$(PPh$_3$)$_2$ (52 mg, 0.045 mmol) and sodium carbonate (96 mg, 0.906 mmol) in aqueous methanol (5 ml) as described in general procedure to give 262 mg of the product as a light yellow solid; ¹H NMR (300 MHz, CDCl$_3$) δ 1.50-1.65 (m, 4H), 1.85-2.00 (m, 4H), 3.84 (s, 3H), 4.89 (br s, 1H), 6.80-6.88 (m, 1H), 6.90-7.10 (m, 4H), 7.54-7.74 (m, 6H), 8.42 (d, J=15.6 Hz, 1H), 8.96 (d, J=7.5 Hz, 1H); ESI-MS: m/z 507.23 [100%, (M+H)⁺].

Example 24

2-{(E)-2-[(2-Cyclopentyloxy-3-methoxy)phenyl]vinyl}-3-(4-trifluoromethoxy)phenyl-4H-pyrido[1,2-a]pyrimidin-4-one

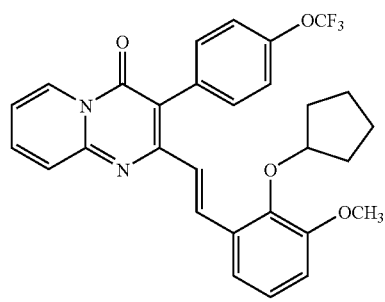

The title compound was prepared by Suzuki coupling reaction of Intermediate 12 (200 mg, 0.453 mmol) with (4-trifluoromethoxy)phenylboronic acid (112 mg, 0.543 mmol) in the presence of PdCl$_2$(PPh$_3$)$_2$ (52 mg, 0.045 mmol) and sodium carbonate (96 mg, 0.906 mmol) in aqueous methanol (5 ml) as described in general procedure to give 292 mg of the product as a light yellow solid; IR (KBr) 2965, 1667, 1261, 1066, 770 cm⁻¹; ¹H NMR (CDCl$_3$) δ 1.60-1.78 (m, 4H), 1.85-2.00 (m, 4H), 3.84 (s, 3H), 4.90 (br s, 1H), 6.84 (d, J=6.9 Hz, 1H), 6.93-7.05 (m, 4H), 7.30 (d, J=8.1 Hz, 2H), 7.47 (d, J=8.7 Hz, 2H), 7.58-7.70 (m, 2H), 8.40 (d, J=15.6 Hz, 1H), 8.96 (d, J=6.9 Hz, 1H); ESI-MS: (m/z) 523.13 (M+H)⁺.

Example 25

2-{(E)-2-[2-(Cyclopentyloxy-3-methoxy)phenyl]vinyl}-3-(3-hydroxy)phenyl-4H-pyrido-[1,2-a]-pyrimidin-4-one

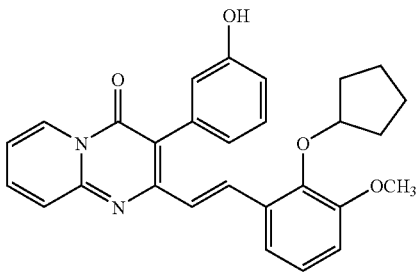 [SMILES: COc1cccc(/C=C/c2nc3ccccn3c(=O)c2-c2cccc(O)c2)c1OC1CCCC1]

The title compound was prepared by Suzuki coupling reaction of Intermediate 12 (200 mg, 0.453 mmol) with 3-hydroxyphenylboronic acid (75 mg, 0.545 mmol) in the presence of PdCl$_2$(PPh$_3$)$_2$ (52 mg, 0.045 mmol) and sodium carbonate (96 mg, 0.906 mmol) in aqueous methanol (4 ml) as described in general procedure to give 267 mg of the product as a light yellow solid; ¹H NMR (300 MHz, CDCl$_3$) δ 1.50-1.60 (m, 4H), 1.85-2.05 (m, 4H), 3.83 (s, 3H), 4.88 (br s, 1H), 5.99 (s, 1H), 6.80-7.00 (m, 6H), 7.30-7.40 (m, 1H), 7.50-7.58 (m, 1H), 7.60-7.70 (m, 2H), 8.39 (d, J=16.2 Hz, 1H), 8.97 (d, J=6.3 Hz, 1H), 9.03 (br s, 1H); ESI-MS: m/z 455.53 [(M+H)+, 100%].

Example 26

2-{(E)-2-[(2-Cyclopentyloxy-3-methoxy)phenyl]vinyl}-3-(3-methoxy)phenyl-4H-pyrido-[1,2-a]pyrimidin-4-one

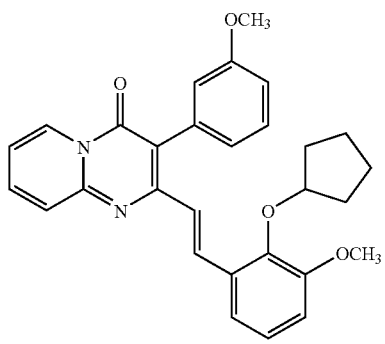 [SMILES: COc1cccc(-c2c(/C=C/c3cccc(OC)c3OC3CCCC3)nc3ccccn3c2=O)c1]

The title compound was prepared by Suzuki coupling reaction of Intermediate 12 (150 mg, 0.341 mmol) with (3-methoxy)phenylboronic acid (62 mg, 0.408 mmol) in in the presence of PdCl$_2$(PPh$_3$)$_2$ (23 mg, 0.034 mmol) and sodium carbonate (72 mg, 0.682 mmol) in aqueous methanol (4 ml) as described in general procedure to give 272 mg of the product as a light yellow solid; IR (KBr) 2959, 1668, 1525, 1258, 968 cm$^{-1}$; $^1$H NMR (300 MHz, CDCl$_3$) δ 1.62-1.70 (m, 4H), 1.92-2.06 (m, 4H), 3.82 (s, 3H), 3.83 (s, 3H), 4.88 (br s, 1H), 6.81 (d, J=7.8 Hz, 1H), 6.93-7.03 (m, 7H), 7.36 (t, J=8.1 Hz, 1H), 7.57-7.67 (m, 2H), 8.38 (d, J=15.6 Hz, 1H), 8.96 (d, J=6.9 Hz, 1H); ESI-MS (m/z) 469.50 (M+H)+.

Example 27

3-(3-Isopropoxyphenyl)-2-[(E)-2-(2-cyclopentyloxy-3-methoxy)phenylvinyl]-4H-pyrido-[1,2-a]pyrimidin-4-one

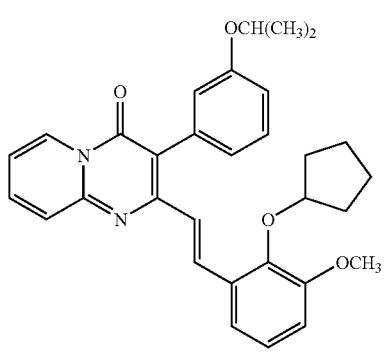

The title compound was prepared by Suzuki coupling reaction of Intermediate 12 (150 mg, 0.341 mmol) with 3-(isopropoxy)phenylboronic acid (73 mg, 0.408 mmol) in the presence of PdCl$_2$(PPh$_3$)$_2$ (23 mg, 0.034 mmol) and sodium carbonate (72 mg, 0.682 mmol) in aqueous methanol (4 ml) as described in general procedure to give 245 mg of the product as a light yellow solid; IR (KBr) 2972, 1659, 1527, 1288, 971 cm$^{-1}$; $^1$H NMR (CDCl$_3$) δ 1.34 (d, J=6.0 Hz, 6H), 1.62-1.68 (m, 4H), 1.93-2.04 (m, 4H), 3.83 (s, 3H), 4.56 (d, J=6.3 Hz, 1H), 4.89 (br s, 1H), 6.81 (d, J=7.5 Hz, 1H), 6.89-7.05 (m, 7H), 7.34 (t, J=7.8 Hz, 1H), 7.57-7.63 (m, 2H), 8.38 (d, J=16.2 Hz, 1H), 8.96 (d, J=7.2 Hz, 1H); ESI-MS: m/z 497.34 (M+H)+.

Example 28

4-{2-[(E)-2-(2-Cyclopentyloxy-3-methoxyphenyl)vinyl]-4-oxo-4H-pyrido[1,2-a]-pyrimidin-3-yl}benzonitrile

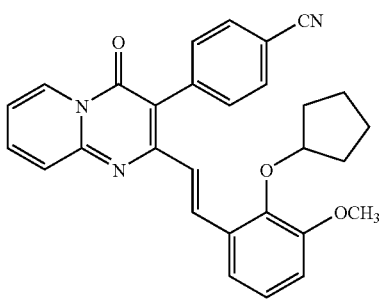

The title compound was prepared by Suzuki coupling reaction of Intermediate 12 (401 mg, 0.906 mmol) with 4-cyanophenylboronic acid (159 mg, 1.087 mmol) in the presence of PdCl$_2$(PPh$_3$)$_2$ (63 mg, 0.090 mmol) and sodium carbonate (192 mg, 1.812 mmol) in aqueous methanol (6 ml) as described in general procedure to give 161 mg of the product as a light yellow solid; IR (KBr) 2958, 2223, 2109, 1637, 1468, 959 cm$^{-1}$; $^1$H NMR (300 MHz, CDCl$_3$) δ 1.62-1.69 (m, 4H), 1.88-1.99 (m, 4H), 3.84 (s, 3H), 4.91 (br s, 1H), 6.80-6.86 (m, 1H), 6.90 (d, J=15.6 Hz, 1H), 6.95-7.02 (m, 2H), 7.07 (t, J=6.9 Hz, 1H), 7.54-7.61 (m, 3H), 7.64-7.73 (m, 3H), 8.42 (d, J=15.6 Hz, 1H), 8.96 (d, J=6.3 Hz, 1H); ESI-MS: m/z 464.64 (M+H)+.

Example 29

4-{4-Oxo-2-[(E)-2-(2-cyclopentyloxy-3-methoxy)phenylvinyl]-4H-pyrido[1,2-a]pyrimidin-3-yl}benzoic acid

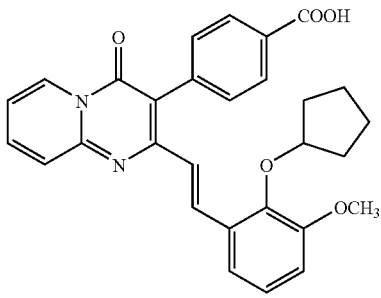

The title compound was prepared by Suzuki coupling reaction of Intermediate 12 (200 mg, 0.453 mmol) with 4-carboxyphenylboronic acid (90 mg, 0.544 mmol) in the presence of PdCl$_2$(PPh$_3$)$_2$ (31 mg, 0.045 mmol) and sodium carbonate (96 mg, 0.906 mmol) in aqueous methanol (5 ml) as described in general procedure to give 274 mg of the product as a light yellow solid; IR (KBr) 3422, 2960, 1709, 1614, 1457, 1213 cm$^{-1}$; $^1$H NMR (300 MHz, DMSO-d$_6$) δ 1.68-1.72 (m, 4H), 1.90-1.95 (m, 4H), 3.78 (s, 3H), 4.68 (br s, 1H), 6.87-7.00 (m, 4H), 7.30 (t, J=8.4 Hz, 1H), 7.50 (d, J=8.4 Hz, 2H), 7.58 (d, J=8.4 Hz, 1H), 7.94 (t, J=8.4 Hz, 1H), 8.02 (d, J=7.8 Hz, 2H), 8.28 (d, J=15.9 Hz, 1H), 8.87 (d, J=6.9 Hz, 1H), 12.99 (br s, 1H); ESI-MS: m/z 481.16 (M−H)$^-$.

Example 30

2-{(E)-2-[(2-Cyclopentyloxy)-3-methoxyphenyl]vinyl}-3-(4-nitro)phenyl-4H-pyrido[1,2-a]pyrimidin-4-one

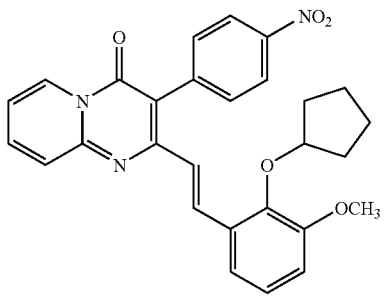

The title compound was prepared by Suzuki coupling reaction of Intermediate 12 (200 mg, 0.453 mmol) with 4-nitrophenylboronic acid (90 mg, 0.543 mmol) in in the presence of PdCl$_2$(PPh$_3$)$_2$ (31 mg, 0.045 mmol) and sodium carbonate (96 mg, 0.906 mmol) in aqueous methanol (5 ml) as described in general procedure to give 222 mg of the product as a light yellow solid; IR (KBr) 2956, 1674, 1510, 1066 cm$^{-1}$; $^1$H NMR (300 MHz, CDCl$_3$) δ 1.62-1.69 (m, 4H), 1.88-2.01 (m, 4H), 3.84 (s, 3H), 4.91 (br s, 1H), 6.83-6.86 (m, 1H), 6.92-6.97 (m, 2H), 7.08 (t, J=6.6 Hz, 1H), 7.63-7.71 (m, 5H), 8.31 (t, J=8.7 Hz, 2H), 8.44 (d, J=15.6 Hz, 1H), 8.97 (d, J=6.9 Hz, 1H); ESI-MS: m/z 483.09 (M)$^+$.

Example 31

N-(3-{2-[(E)-2-(2-Cyclopentyloxy-3-methoxy)phenylvinyl]-4-oxo-4H-pyrido[1,2-a]pyrimidin-3-yl}phenyl)acetamide

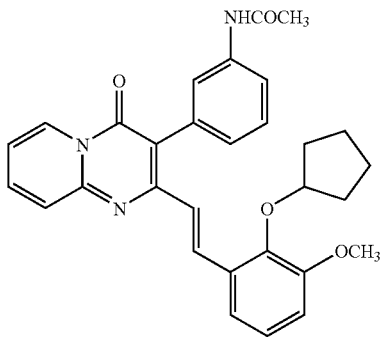

The title compound was prepared by Suzuki coupling reaction of Intermediate 12 (150 mg, 0.341 mmol) with 3-acetamidophenylboronic acid (73 mg, 0.408 mmol) in the presence of PdCl$_2$(PPh$_3$)$_2$ (23 mg, 0.034 mmol) and sodium carbonate (72 mg, 0.683 mmol) in aqueous methanol (5 ml) as described in general procedure to give 307 mg of the product as a light yellow solid; IR (KBr) 3279, 3086, 2957, 1650, 1619, 1525, 1261, 1069 cm$^{-1}$; $^1$H NMR (300 MHz, CDCl$_3$) δ 1.63-1.69 (m, 4H), 1.92-1.96 (m, 4H), 2.07 (s, 3H), 3.83 (s, 3H), 4.88 (br s, 1H), 6.81 (d, J=7.8 Hz, 1H), 6.90-7.03 (m, 4H), 7.07 (d, J=7.8 Hz, 1H), 7.27 (s, 1H), 7.39 (t, J=7.8 Hz, 1H), 7.59-7.65 (m, 3H), 7.82 (d, J=7.8 Hz, 1H), 8.40 (d, J=15.6 Hz, 1H), 8.95 (d, J=7.5 Hz, 1H); ESI-MS: m/z 496.18 (M+H)$^+$.

Example 32

N-(4-{2-[(E)-2-(2-Cyclopentyloxy-3-methoxy)phenylvinyl]-4-Oxo-4H-pyrido[1,2-a]pyrimidin-3-yl}phenyl)acetamide

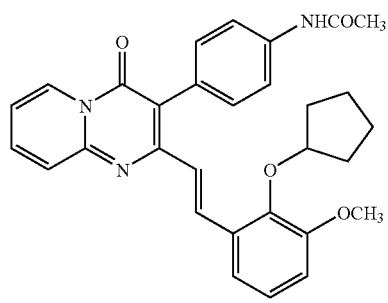

The title compound was prepared by Suzuki coupling reaction of Intermediate 12 (200 mg, 0.453 mmol) with 4-acetamidophenylboronic acid (97 mg, 0.544 mmol) in the presence of PdCl$_2$(PPh$_3$)$_2$ (31 mg, 0.045 mmol) and sodium carbonate (96 mg, 0.906 mmol) in aqueous methanol (5 ml) as described in general procedure to give 298 mg of the product as a light yellow solid; IR (KBr) 3279, 3086, 2957, 1650, 1619, 1525, 1261, 1069 cm$^{-1}$; $^1$H NMR (300 MHz, CDCl$_3$) δ 1.63-1.69 (m, 4H), 1.92-1.96 (m, 4H), 2.07 (s, 3H), 3.83 (s, 3H), 4.88 (br s, 1H), 6.81-6.89 (m, 1H), 6.90-6.99 (m, 3H), 7.05 (d, J=6.3 Hz, 1H), 7.59-7.69 (m, 5H), 7.82 (d, J=7.8 Hz, 2H), 8.40 (d, J=15.6 Hz, 1H), 8.95 (d, J=7.5 Hz, 1H); ESI-MS: m/z 496.18 (M+H)$^+$.

Example 33

3-(4-Acetylphenyl)-2-[(E)-2-(2-cyclopentyloxy-3-methoxy)phenylvinyl]-4H-pyrido[1,2-a]pyrimidin-4-one

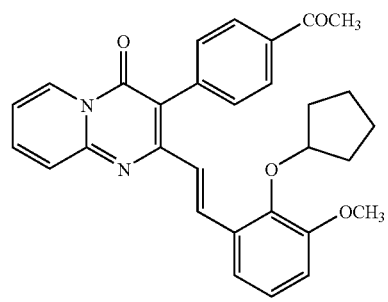 [SMILES: COc1cccc(/C=C/c2nc3ccccn3c(=O)c2-c2ccc(C(C)=O)cc2)c1OC1CCCC1]

The title compound was prepared by Suzuki coupling reaction of Intermediate 12 (150 mg, 0.341 mmol) with 4-acetylphenylboronic acid (66 mg, 0.408 mmol) in the presence of PdCl$_2$(PPh$_3$)$_2$ (23 mg, 0.034 mmol) and sodium carbonate (72 mg, 0.683 mmol) in aqueous methanol (4 ml) as described in general procedure to give 305 mg of the product as a light yellow solid; IR (KBr) 2964, 1666, 1451, 1265, 1066 cm$^{-1}$; $^1$H NMR (300 MHz, CDCl$_3$) δ 1.63-1.69 (m, 4H), 1.92-2.02 (m, 4H), 2.67 (s, 3H), 3.84 (s, 3H), 4.89 (br s, 1H), 6.86-7.05 (m, 5H), 7.57-7.68 (m, 4H), 8.04 (d, J=8.1 Hz, 2H), 8.42 (d, J=15.6 Hz, 1H), 8.97 (d, J=6.9 Hz, 1H); ESI-MS: m/z 481.29 (M+H)$^+$.

Example 34

2-{(E)-2-[(2-Cyclopentyloxy-3-methoxy)phenyl]vinyl}-3-(4-thiomethyl)phenyl-4H-pyrido[1,2-a]pyrimidin-4-one

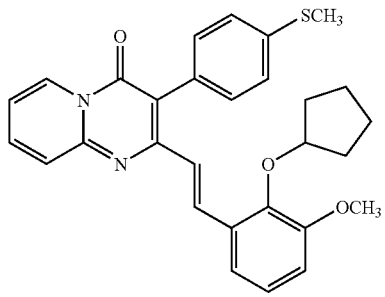 [SMILES: COc1cccc(/C=C/c2nc3ccccn3c(=O)c2-c2ccc(SC)cc2)c1OC1CCCC1]

The title compound was prepared by Suzuki coupling reaction of Intermediate 12 (150 mg, 0.341 mmol) with (4-thiomethyl)phenylboronic acid (68 mg, 0.408 mmol) in the presence of PdCl$_2$(PPh$_3$)$_2$ (23 mg, 0.034 mmol) and sodium carbonate (72 mg, 0.683 mmol) in aqueous methanol (5 ml) as described in general procedure to give 302 mg of the product as a light yellow solid; IR (KBr) 2954, 1666, 1451, 1066, 770 cm$^{-1}$; $^1$H NMR (300 MHz, CDCl$_3$) δ 1.64-1.70 (m, 4H), 1.92-2.06 (m, 4H), 2.54 (s, 3H), 3.84 (s, 3H), 4.90 (br s, 1H), 6.83 (d, J=7.2 Hz, 1H), 6.95-7.07 (m, 3H), 7.33-7.39 (m, 4H), 7.60-7.66 (m, 3H), 8.38 (d, J=16.2 Hz, 1H), 8.96 (d, J=6.3 Hz, 1H); ESI-MS: m/z 485.31 (M+H)$^+$.

Example 35

2-{(E)-2-[2-(Cyclopentyloxy)-3-methoxyphenyl]vinyl}-3-pyridin-4-yl-4H-pyrido[1,2-a]-pyrimidin-4-one

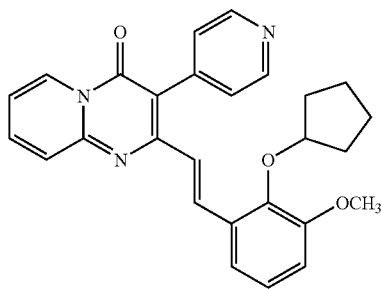

The title compound was prepared by Suzuki coupling reaction of Intermediate 12 (200 mg, 0.453 mmol) with 4-pyridineboronic acid (66 mg, 0.541 mmol) in the presence of PdCl$_2$(PPh$_3$)$_2$ (31 mg, 0.044 mmol) in dioxane (15 ml) and sodium carbonate (96 mg, 0.914 mmol) in water (3 ml) as described in general procedure give 276 mg of the product as a light yellow solid; IR (KBr) 2958, 2358, 1672, 1633, 1498, 1263, 1068, 770 cm$^{-1}$; $^1$H NMR (300 MHz, CDCl$_3$) δ 1.20-1.30 (m, 4H), 1.85-2.10 (m, 4H), 3.85 (s, 3H), 4.91 (br s, 1H), 6.82-6.90 (m, 1H), 6.92-7.01 (m, 3H), 7.02-7.12 (m, 1H), 7.38-7.44 (m, 2H), 7.60-7.76 (m, 2H), 8.45 (d, J=15.9 Hz, 1H), 8.71 (d, J=6.0 Hz, 2H), 8.97 (d, J=7.2 Hz, 1H); ESI-MS: m/z 440.27 [100%, (M+H)$^+$].

Example 36

2-{(E)-2-[2-(Cyclopentyloxy-3-methoxy)phenyl]vinyl}-3-(6-fluoro)pyridin-3-yl-4H-pyrido[1,2-a]pyrimidin-4-one

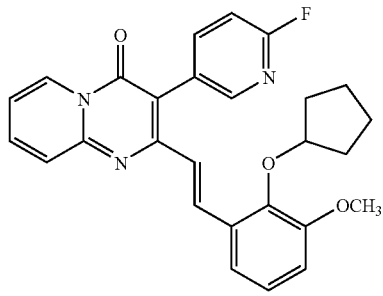 [SMILES: COc1cccc(/C=C/c2nc3ccccn3c(=O)c2-c2ccc(F)nc2)c1OC1CCCC1]

The title compound was prepared by Suzuki coupling reaction of Intermediate 12 (200 mg, 0.453 mmol) with 2-fluoro-5-pyridylboronic acid (76 mg, 0.543 mmol) in the presence of Pd(PPh$_3$)$_4$ (52 mg, 0.045 mmol) and sodium carbonate (96 mg, 0.906 mmol) in aqueous methanol (6 ml) as described in general procedure to give 295 mg of the product as a light yellow solid; IR (KBr) 2958, 1668, 1526, 1259, 1067 cm$^{-1}$; $^1$H NMR (300 MHz, CDCl$_3$) δ 1.60-1.76 (m, 4H), 1.84-2.05 (m, 4H), 3.84 (s, 3H), 4.91 (br s, 1H), 6.84-7.05 (m, 6H), 7.62 (d, J=8.7 Hz, 1H), 7.69 (d, J=6.9 Hz, 1H), 7.92 (t, J=6.6 Hz, 1H), 8.26 (s, 1H), 8.45 (d, J=15.0 Hz, 1H), 8.95 (d, J=7.2 Hz, 1H); ESI-MS: m/z 458.43 (M+H)$^+$.

Example 37

3-(1,3-Benzodioxol-5-yl)-2-[(E)-2-(2-cyclopentyloxy-3-methoxy)phenylvinyl]-4H-pyrido[1,2-a]pyrimidin-4-one

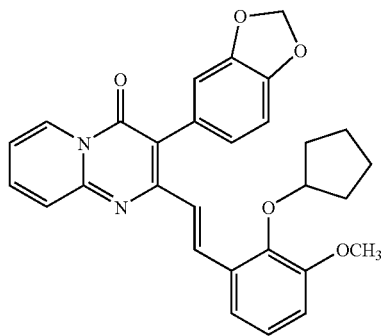 [SMILES: COc1cccc(/C=C/c2nc3ccccn3c(=O)c2-c2ccc3c(c2)OCO3)c1OC1CCCC1]

The title compound was prepared by Suzuki coupling reaction of Intermediate 12 (150 mg, 0.341 mmol) with 3,4-(methylenedioxy)phenylboronic acid (67 mg, 0.408 mmol) in the presence of PdCl$_2$(PPh$_3$)$_2$ (23 mg, 0.034 mmol) and sodium carbonate (72 mg, 0.683 mmol) in aqueous methanol (5 ml) as described in general procedure to give 256 mg of the product as a light yellow solid; IR (KBr) 2953, 1660, 1528, 1249, 1034 cm$^{-1}$; $^1$H NMR (300 MHz, CDCl$_3$) δ 1.63-1.69 (m, 4H), 1.92-2.02 (m, 4H), 3.84 (s, 3H), 4.89 (br s, 1H), 6.01 (s, 2H), 6.86-7.05 (m, 8H), 7.57-7.68 (m, 2H), 8.36 (d, J=15.6 Hz, 1H), 8.95 (d, J=7.2 Hz, 1H); ESI-MS (m/z) 482.32 (M+H)$^+$.

Example 38

2-[(E)-2-(2-Cyclopentyloxy-3-methoxy)phenylvinyl]-3-quinolin-6-yl-4H-pyrido[1,2-a]pyrimidin-4-one

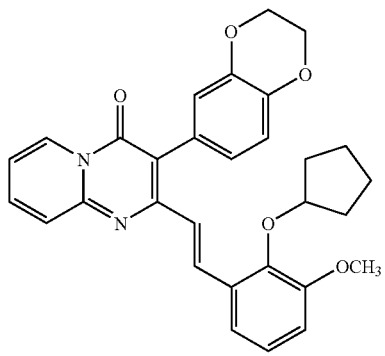 [SMILES: COc1cccc(/C=C/c2nc3ccccn3c(=O)c2-c2ccc3c(c2)OCCO3)c1OC1CCCC1]

The title compound was prepared by Suzuki coupling reaction of Intermediate 12 (150 mg, 0.341 mmol) with 1,4-benzodioxane-6-boronic acid (73 mg, 0.408 mmol) in the presence of PdCl$_2$(PPh$_3$)$_2$ (23 mg, 0.034 mmol) and sodium carbonate (72 mg, 0.683 mmol) in aqueous methanol (30 ml) as described in general procedure to give 263 mg of the product as a light yellow solid; IR (KBr) 2954, 1660, 1508, 1304, 1064 cm$^{-1}$; $^1$H NMR (CDCl$_3$) δ 1.63-1.69 (m, 4H), 1.92-2.02 (m, 4H), 3.84 (s, 3H), 4.30 (s, 4H), 4.90 (br s, 1H), 6.81-6.89 (m, 2H), 6.92-7.08 (m, 6H), 7.59-7.63 (m, 2H), 8.36 (d, J=15.6 Hz, 1H), 8.95 (d, J=6.3 Hz, 1H); ESI-MS: m/z 497.19 (M+H)$^+$.

Example 39

2-[(E)-2-(2-Cyclopentyloxy-3-methoxy)phenylvinyl]-3-quinolin-7-yl-4H-pyrido[1,2-a]pyrimidin-4-one

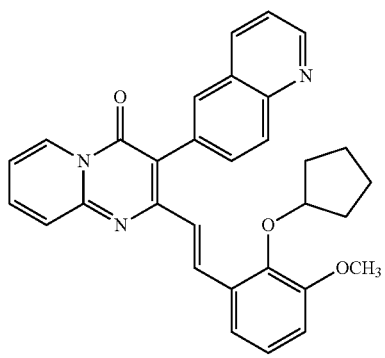 [SMILES: COc1cccc(/C=C/c2nc3ccccn3c(=O)c2-c2ccc3ncccc3c2)c1OC1CCCC1]

The title compound was prepared by Suzuki coupling reaction of Intermediate 12 (200 mg, 0.453 mmol) with 6-quinolineboronic acid (138 mg, 0.544 mmol) in the presence of PdCl$_2$(PPh$_3$)$_2$ (31 mg, 0.045 mmol) and sodium carbonate (96 mg, 0.906 mmol) in aqueous methanol (6 ml) as described in general procedure to give 303 mg of the product as a light yellow solid; $^1$H NMR (300 MHz, CDCl$_3$) δ 1.59-1.69 (m, 4H), 1.88-1.96 (m, 4H), 3.80 (s, 3H), 4.87 (br s, 1H), 6.79-6.89 (m, 3H), 6.90-7.06 (m, 2H), 7.32-7.39 (m, 2H), 7.60-7.66 (m, 2H), 7.76 (d, J=7.8 Hz, 1H), 7.90 (s, 1H), 8.15 (br s, 2H), 8.42 (d, J=15.6 Hz, 1H), 8.92-8.98 (m, 2H); ESI-MS: m/z 490.30 (M+H)$^+$.

Example 40

2-{(E)-2-[(2-Cyclopentyloxy-3-methoxy)phenyl]vinyl}-9-methyl-3-(4-trifluoromethyl)phenyl-4H-pyrido[1,2-a]pyrimidin-4-one

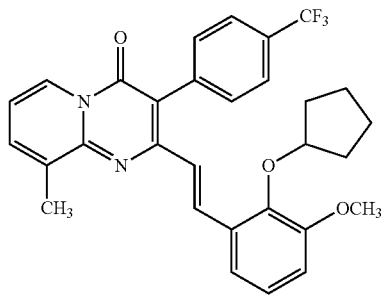 [SMILES: COc1cccc(/C=C/c2nc3c(C)cccn3c(=O)c2-c2ccc(C(F)(F)F)cc2)c1OC1CCCC1]

The title compound was prepared by Suzuki coupling reaction of Intermediate 13 (300 mg, 1.857 mmol) with 4-trifluoromethylphenylboronic acid (272 mg, 1.422 mmol) in the presence of PdCl$_2$(PPh$_3$)$_2$ (83 mg, 0.118 mmol) and sodium carbonate (251 mg, 2.371 mmol) in aqueous methanol (10 ml) as described in general procedure to give 270 mg of the product as a light yellow solid; $^1$H NMR (300 MHz, CDCl$_3$) δ 1.62-1.70 (m, 4H), 1.80-1.90 (m, 2H), 2.70 (s, 3H), 3.84 (s, 3H), 4.87 (br s, 1H), 6.88-7.00 (m, 5H), 7.56 (d, J=6.3 Hz, 3H), 7.71 (d, J=6.9 Hz, 2H), 8.42 (d, J=15.6 Hz, 1H), 8.96 (d, J=6.9 Hz, 1H).

Example 41

4-{2-[(E)-2-(2-Cyclopentyloxy-3-methoxyphenyl)vinyl]-9-methoxy-4-oxo-4H-pyrido[1,2-a]pyrimidin-3-yl}benzonitrile

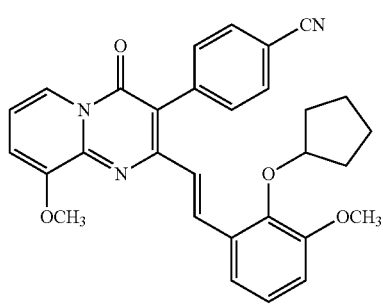 [SMILES: COc1cccc(/C=C/c2nc3c(OC)cccn3c(=O)c2-c2ccc(C#N)cc2)c1OC1CCCC1]

The title compound was prepared by Suzuki coupling reaction of Intermediate 14 (200 mg, 4.243 mmol) with 4-cyanophenylboronic acid (74 mg, 0.509 mmol) in the presence of PdCl$_2$(PPh$_3$)$_2$ (29 mg, 0.042 mmol) and sodium carbonate (89 mg, 0.848 mmol) in aqueous methanol (8 ml) as described in general procedure to give 208 mg of the product as a light yellow solid; $^1$H NMR (300 MHz, CDCl$_3$) δ 1.60-1.77 (m, 4H), 1.88-1.99 (m, 4H), 3.83 (s, 3H), 4.06 (s, 3H), 4.90 (br s, 1H), 6.88-7.02 (m, 6H), 7.57 (d, J=7.8 Hz, 2H), 7.74 (d, J=7.8 Hz, 2H), 8.44 (d, J=15.6 Hz, 1H), 8.60 (br s, 1H); APCI-MS: m/z 493.20 (M)$^+$.

Example 42

4-{7-Chloro-2-[(E)-2-[(2-Cyclopropylmethoxy-3-methoxyphenyl)vinyl]-4-oxo-4H-pyrido[1,2-a]pyrimidin-3-yl}benzonitrile

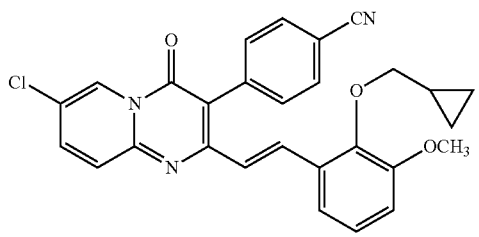 [SMILES: COc1cccc(/C=C/c2nc3ccc(Cl)cn3c(=O)c2-c2ccc(C#N)cc2)c1OCC1CC1]

The title compound was prepared by Suzuki coupling reaction of Intermediate 15 (110 mg, 0.238 mmol) with 4-cyanophenylboronic acid (42 mg, 0.285 mmol) in the presence of PdCl$_2$(PPh$_3$)$_2$ (29 mg, 0.023 mmol) and sodium carbonate (50 mg, 0.472 mmol) in aqueous methanol (30 ml) as described in general procedure to give 278 mg of the product as a light yellow solid; IR (KBr) 2972, 2223, 1637, 1225, 759 cm$^{-1}$; $^1$H NMR (300 MHz, CDCl$_3$) δ 0.30-0.36 (m, 2H), 0.59 (d, J=6.9 Hz, 2H), 1.20 (brs, 1H), 3.80 (d, J=6.9 Hz, 2H), 3.84 (s, 3H), 6.81 (d, J=7.2 Hz, 1H), 6.93-6.99 (m, 3H), 735-7.40 (m, 1H), 7.54-7.62 (m, 4H), 7.75 (d, J=8.4 Hz, 2H), 8.44 (d, J=15.9 Hz, 1H), 8.97 (d, J=6.9 Hz, 1H); APCI-MS: m/z 483.13 (M)$^+$.

Example 43

4-{7-Chloro-2-[(E)-2-(2-cyclopentyloxy-3-methoxy)phenylvinyl]-4-oxo-4H-pyrido[1,2-a]pyrimidin-3-yl}benzonitrile

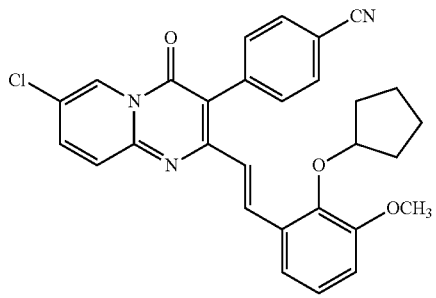 [SMILES: COc1cccc(/C=C/c2nc3ccc(Cl)cn3c(=O)c2-c2ccc(C#N)cc2)c1OC1CCCC1]

The title compound was prepared by Suzuki coupling reaction of Intermediate 16 (200 mg, 0.426 mmol) with 4-cyanophenylboronic acid (74 mg, 0.503 mmol) in the presence of PdCl$_2$(PPh$_3$)$_4$ (29 mg, 0.042 mmol) and sodium carbonate (89 mg, 0.841 mmol) in aqueous methanol (30 ml) as described in general procedure to give 115 mg of the product as a light yellow solid; IR (KBr) 2957, 2226, 1650, 1525, 1261, 1069 cm$^{-1}$; $^1$H NMR (300 MHz, CDCl$_3$) δ 1.63-1.69 (m, 4H), 1.88-1.96 (m, 4H), 3.84 (s, 3H), 4.91 (br s, 1H), 6.81-6.89 (m, 4H), 7.54-7.66 (m, 4H), 7.75 (d, J=7.8 Hz, 2H), 8.41 (d, J=15.6 Hz, 1H), 8.95 (s, 1H); ESI-MS: m/z 498.34 (M+H)$^+$.

Pharmacological Activity

The illustrative examples of the present invention are screened for TRPV3 activity according to a modified procedure described in Tóth, A., Kedei, N., Wang, Y. and Blumberg, P. M. *Life Sciences* (2003), 73, 487-498. The screening of the compounds can be carried out by other methods and procedures known to a person skilled in the art. Such screening methods may be found in (a) Hu, H.-Z. et al. *J. Biol. Chem.* (2004), 279, 35741-35747; (b) Smith, G. D. et al. *Nature* (2002), 418, 186-190; (c) Peier, A. M. et al. *Science* (2002), 296, 2046-2049.

Screening for TRPV3 Antagonist Using the $^{45}$Calcium Uptake Assay:

The inhibition of TRPV3 receptor activation was followed as inhibition of 2-aminoethxydiphenylborate (2-APB) induced cellular uptake of radioactive calcium. Test compounds were dissolved in dimethyl sulfoxide (DMSO) to prepare 20 mM stock solution and then diluted using plain medium with DMEM/F-12 containing 1.8 mM CaCl$_2$ to get desired concentration. Final concentration of DMSO in the reaction was 0.5% (v/v). Human TRPV3 expressing CHO cells were grown in DMEM/F-12 medium with 10% FBS, 1% penicillin-streptomycin solution, 400 µg/ml of G-418. Cells were seeded 24 h prior to the assay in 96 well plates so as to get ~50,000 cells per well on the day of experiment. Cells were treated with test compounds for 10 minutes followed by addition of 2-APB at a final concentration of 500 µM and 5 µCi/ml $^{45}$Ca$^{+2}$ for 4 minutes. Cells were washed and lysed using buffer containing 1% Triton X-100, 0.1% deoxycholate and 0.1% SDS. Radioactivity in the lysate was measured in Packardt Top count after addition of liquid scintillant. Concentration response curves were plotted as a % of maximal response obtained in the absence of test antagonist. IC$_{50}$ value was calculated from concentration response curve by nonlinear regression analysis using GraphPad PRISM software.

The compounds prepared were tested using the above assay procedure and the results obtained are given in Table 1. Percentage inhibition at concentrations of 1.0 µM and 10.0 µM are given in the table along with IC$_{50}$ (nM) values for selected examples.

The IC$_{50}$ (nM) values of the compounds are set forth in Table 1 wherein "A" refers to an IC$_{50}$ value of less than 500 nM, "B" refers to IC$_{50}$ value in range of 500.1 to 1000.0 nM and "C" refers to an IC$_{50}$ value in range of 1000.1 to 2500.0 nM.

TABLE 1

In-vitro screening results of compounds of invention

| Examples | Percentage inhibition | | IC$_{50}$ value (nM) |
| --- | --- | --- | --- |
| | at 1.0 µM | at 10.0 µM | |
| Example 1 | 0.5 | 19.4 | — |
| Example 2 | 5.7 | 11.2 | — |
| Example 3 | 14.4 | 77.9 | C |
| Example 4 | 25.3 | 74.0 | — |

TABLE 1-continued

In-vitro screening results of compounds of invention

| Examples | Percentage inhibition at 1.0 μM | at 10.0 μM | IC$_{50}$ value (nM) |
|---|---|---|---|
| Example 5 | 41.6 | 76.2 | — |
| Example 6 | 71.5 | 67.5 | — |
| Example 7 | 77.9 | 98.9 | — |
| Example 8 | 76.3 | 89.7 | — |
| Example 9 | 74.6 | 89. | B |
| Example 10 | 82.82 | 100.0 | — |
| Example 11 | 69.0 | 86.5 | — |
| Example 12 | 87.9 | 96.5 | A |
| Example 13 | 58.0 | 77.3 | — |
| Example 14 | 85.1 | 92.3 | A |
| Example 15 | 0.0 | 31.7 | — |
| Example 16 | 33.8 | 79.8 | — |
| Example 17 | 83.3 | 95.3 | A |
| Example 18 | 79.5 | 93.5 | A |
| Example 19 | 87.8 | 98.7 | A |
| Example 20 | 45.9 | 76.7 | C |
| Example 21 | 27.2 | 39.3 | — |
| Example 22 | 22.7 | 34.6 | — |
| Example 23 | 62.8 | 86.7 | B |
| Example 24 | 20.6 | 3.6 | C |
| Example 25 | 20.7 | 93.1 | C |
| Example 26 | 48.0 | 69.3 | — |
| Example 27 | 54.2 | 77.6 | C |
| Example 28 | 83.5 | 94.7 | A |
| Example 29 | 0.0 | 0.2 | — |
| Example 30 | 52.0 | 76.4 | — |
| Example 31 | 50.4 | 96.2 | — |
| Example 32 | 34.2 | 89.6 | — |
| Example 33 | 78.0 | 94.3 | A |
| Example 34 | 36.8 | 51.3 | — |
| Example 35 | 18.4 | 63.3 | — |
| Example 36 | 42.2 | 82.4 | B |
| Example 37 | 70.1 | 91.4 | — |
| Example 38 | 55.5 | 83.8 | A |
| Example 39 | 84.6 | 96.1 | A |
| Example 40 | 23.1 | 18.7 | — |
| Example 41 | 54.8 | 87.6 | — |
| Example 42 | 0.0 | 96.8 | — |
| Example 43 | 78.7 | 90.2 | A |

The invention claimed is:

1. The compound of formula (I):

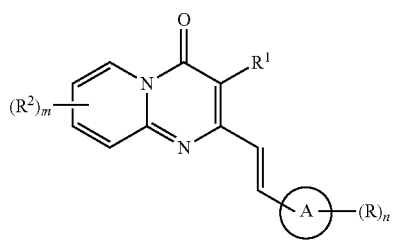

(I)

wherein,
ring A is aryl or heteroaryl;
R is nitro, cyano, halogen, —OR$^a$, substituted or unsubstituted alkyl, haloalkyl, substituted or unsubstituted cycloalkyl, substituted or unsubstituted aryl, substituted or unsubstituted heterocyclic group or substituted or unsubstituted heteroaryl;
R$^1$ is nitro, cyano, halogen, substituted or unsubstituted cycloalkyl, substituted or unsubstituted cycloalkenyl, substituted or unsubstituted aryl, substituted or unsubstituted heteroaryl, substituted or unsubstituted heterocyclic group, —NR$^3$R$^4$, —C(O)—R$^3$, —C(O)O—R$^3$, —C(O)NR$^3$R$^4$, —S(O)$_p$NR$^3$R$^4$ or —S(O)$_p$R$^3$; wherein substituents of aryl, heteroaryl or heterocyclic group are independently selected from halogen, nitro, cyano, —COOH, —C(O)—R$^3$, —NHC(O)—R$^3$, —OR$^a$, substituted or unsubstituted alkyl, linear or branched chain alkyl, haloalkyl, thioalkyl or substituted or unsubstituted cycloalkyl;
R$^2$ is hydrogen, nitro, cyano, halogen, —OR$^a$, substituted or unsubstituted alkyl, substituted or unsubstituted cycloalkyl, substituted or unsubstituted cycloalkenyl, substituted or unsubstituted aryl, substituted or unsubstituted heteroaryl, substituted or unsubstituted heterocyclic group, —NR$^3$R$^4$, —C(O)NR$^3$R$^4$, —S(O)$_p$NR$^3$R$^4$ or —S(O)$_p$R$^3$;
each occurrence of R$^a$ is independently selected from the group consisting of hydrogen, substituted or unsubstituted alkyl, haloalkyl, substituted or unsubstituted alkenyl, substituted or unsubstituted cycloalkyl, substituted or unsubstituted aryl, substituted or unsubstituted heteroaryl, substituted or unsubstituted heterocyclic group, substituted or unsubstituted cycloalkylalkyl, substituted or unsubstituted arylalkyl, substituted or unsubstituted heteroarylalkyl or substituted or unsubstituted heterocyclylalkyl;
each occurrence of R$^3$ and R$^4$ are independently hydrogen, —OR$^a$, substituted or unsubstituted alkyl, substituted or unsubstituted alkenyl, substituted or unsubstituted cycloalkyl, substituted or unsubstituted cycloalkylalkyl, substituted or unsubstituted cycloalkenyl substituted or unsubstituted aryl, substituted or unsubstituted arylalkyl, substituted or unsubstituted heteroaryl, substituted or unsubstituted heteroarylalkyl, substituted or unsubstituted heterocyclic group or substituted or unsubstituted heterocyclylalkyl;
'm' is an integer selected from 0 to 4;
'n' is an integer selected from 0 to 5;
'p' is an integer selected from 0 to 2;
or stereoisomer, enantiomer, diastereomer or pharmaceutically acceptable salt thereof.

2. The compound according to claim 1, wherein R$^1$ is substituted or unsubstituted aryl, substituted or unsubstituted heteroaryl or substituted or unsubstituted heterocyclic group.

3. The compound according to claim 1, wherein ring 'A' is aryl.

4. The compound according to claim 1, as represented by formula (II);

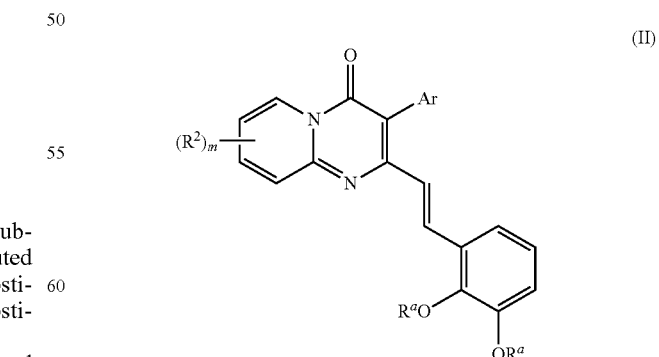

(II)

wherein,
Ar is substituted or unsubstituted aryl, substituted or unsubstituted heteroaryl or substituted or unsubstituted heterocyclic group; wherein substituents of aryl, heteroaryl or heterocyclic group are independently selected from halogen, nitro, cyano, —COOH, —C(O)—$R^3$, —NHC(O)—$R^3$, —$OR^a$, substituted or unsubstituted alkyl, linear or branched chain alkyl, haloalkyl, thioalkyl or substituted or unsubstituted cycloalkyl;

$R^2$ is hydrogen, nitro, cyano, halogen, —$OR^a$, substituted or unsubstituted alkyl, substituted or unsubstituted cycloalkyl, substituted or unsubstituted cycloalkenyl, substituted or unsubstituted aryl, substituted or unsubstituted heteroaryl, substituted or unsubstituted heterocyclic group, —$NR^3R^4$, —C(O)$NR^3R^4$, —$S(O)_pNR^3R^4$ or —$S(O)_pR^3$;

each occurrence of $R^a$ is independently selected from the group consisting of hydrogen, substituted or unsubstituted alkyl, haloalkyl, substituted or unsubstituted alkenyl, substituted or unsubstituted cycloalkyl, substituted or unsubstituted aryl, substituted or unsubstituted heteroaryl, substituted or unsubstituted heterocyclic group, substituted or unsubstituted cycloalkylalkyl, substituted or unsubstituted arylalkyl, substituted or unsubstituted heteroarylalkyl or substituted or unsubstituted heterocyclylalkyl;

each occurrence of $R^3$ and $R^4$ are independently hydrogen, —$OR^a$, substituted or unsubstituted alkyl, substituted or unsubstituted alkenyl, substituted or unsubstituted cycloalkyl, substituted or unsubstituted cycloalkylalkyl, substituted or unsubstituted cycloalkenyl substituted or unsubstituted aryl, substituted or unsubstituted arylalkyl, substituted or unsubstituted heteroaryl, substituted or unsubstituted heteroarylalkyl, substituted or unsubstituted heterocyclic group or substituted or unsubstituted heterocyclylalkyl;

'm' is an integer selected from 0 to 4;
'p' is an integer selected from 0 to 2;
or stereoisomer, enantiomer, diastereomer or pharmaceutically acceptable salt thereof.

5. The compound according to claim 4, wherein Ar is substituted or unsubstituted aryl.

6. The compound according to claim 5, wherein aryl is unsubstituted phenyl.

7. The compound according to claim 5, wherein aryl is substituted phenyl.

8. The compound according to claim 4, wherein Ar is substituted or unsubstituted heteroaryl or heterocyclic group.

9. The compound according to claim 8, wherein heteroaryl is substituted pyridine.

10. The compound according to claim 8, wherein heteroaryl is unsubstituted pyridine or quinoline.

11. The compound according to claim 8, wherein heterocyclic group is benzodioxole or benzodioxine.

12. The compound according to claim 5, wherein one or more substituents on the aryl group is selected from the group consisting of fluorine, hydroxyl, cyano, COOH, —C(O)$CH_3$, nitro, methoxy, isopropoxy, trifluoromethyl, trifluoromethoxy, thiomethyl or —NHC(O)$CH_3$.

13. The compound according to claim 4, wherein each of $R^a$ is independently selected from alkyl, cycloalkyl, cycloalkylalkyl or dialkylaminoalkyl.

14. The compound according to claim 13, wherein alkyl is methyl, propyl, n-butyl, n-pentyl or n-hexyl.

15. The compound according to claim 13, wherein cycloalkyl is cyclopentyl.

16. The compound according to claim 13, wherein cycloalkylalkyl is cyclopropylmethyl.

17. The compound according to claim 13, wherein dialkylaminoalkyl is —$CH_2CH_2N(CH_3)_2$.

18. The compound according to claim 1, wherein 'm' is 0.

19. The compound according to claim 1, wherein $R^2$ is cloro or methoxy when 'm' is 1.

20. The compound according to claim 1, wherein ring 'A' is heteroaryl.

21. The compound according to claim 20, wherein heteroaryl is thienyl or pyridine.

22. The compound according to claim 1, selected from the group consisting of,

2-[(E)-2-(4-Chlorophenyl)vinyl]-3-phenyl-4H-pyrido[1,2-a]pyrimidin-4-one,

2-{(E)-2-(Pyridin-3-yl)vinyl}-3-(4-trifluoromethyl)phenyl-4H-pyrido[1,2-a]pyrimidin-4-one, 2-[(E)-2-(2-Thienyl)vinyl]-3-[4-(trifluoromethyl)phenyl]-4H-pyrido[1,2-a]pyrimidin-4-one, 4-{2-[(E)-2-[2-(Cyclopentyloxy)-3-methoxyphenyl)vinyl]-4-oxo-4H-pyrido[1,2-a]pyrimidin-3-yl}benzonitrile, 2-[(E)-2-[(3-Methoxy-2-propoxyphenyl)vinyl]-3-[4-(trifluoromethyl)phenyl]-4H-pyrido[1,2-a]pyrimidin-4-one, 4-{2-[(E)-2-[(3-Methoxy-2-propoxyphenyl)vinyl]-4-oxo-4H-pyrido[1,2-a]pyrimidin-3-yl}benzonitrile, 2-[(E)-2-[(2-Butoxy-3-methoxyphenyl)vinyl]-3-[4-(trifluoromethyl)phenyl]-4H-pyrido[1,2-a]pyrimidin-4-one, 2-[(E)-2-[2-Butoxy-3-methoxyphenyl)vinyl]-3-[4-(trifluoromethoxy)phenyl]-4H-pyrido[1,2-a]pyrimidin-4-one, 4-{2-[(E)-2-[(2-Butoxy-3-methoxyphenyl)vinyl]-4-oxo-4H-pyrido[1,2-a]pyrimidin-3-yl}benzonitrile, 2-[(E)-2-[(3-Methoxy-2-pentyloxyphenyl)vinyl]-3-[4-(trifluoromethyl)phenyl]-4H-pyrido[1,2-a]pyrimidin-4-one, 4-{2-[(E)-2-[3-Methoxy-2-pentyloxyphenyl)vinyl]-4-oxo-4H-pyrido[1,2-a]pyrimidin-3-yl}benzonitrile, 2-[(E)-2-[(2-Hexyloxy-3-methoxyphenyl)vinyl]-3-[4-(trifluoromethyl)phenyl]-4H-pyrido[1,2-a]pyrimidin-4-one, 4-{2-[(E)-2-[(2-Hexyloxy-3-methoxyphenyl)vinyl]-4-oxo-4H-pyrido[1,2-a]pyrimidin-3-yl}benzonitrile, 2-[(E)-2-{2-[2-(Dimethylamino)ethoxy]-3-methoxyphenyl}vinyl]-3-(4-trifluoromethylphenyl)-4H-pyrido[1,2-a]pyrimidin-4-one hydrochloride, 2-{(E)-2-[2-(Cyclopropylmethoxy)-3-methoxyphenyl]vinyl}-3-phenyl-4H-pyrido[1,2-a]-pyrimidin-4-one, 2-[(E)-2-[(2-Cyclopropylmethoxy-3-methoxyphenyl)vinyl]-3-[4-(trifluoromethyl)phenyl]-4H-pyrido[1,2-a]pyrimidin-4-one, 2-[(E)-2-[(2-Cyclopropylmethoxy-3-methoxyphenyl)vinyl]-3-[4-(trifluoro-methoxy)phenyl]-4H-pyrido[1,2-a]pyrimidin-4-one, 4-{2-[(E)-2-[(2-Cyclopropylmethoxy-3-methoxyphenyl)vinyl]-4-oxo-4H-pyrido[1,2-a]pyrimidin-3-yl}benzonitrile, 2-{(E)-2-[2-(Cyclopentyloxy)-3-methoxyphenyl]vinyl}-3-phenyl-4H-pyrido[1,2-a]-pyrimidin-4-one, 2-{(E)-2-[2-(Cyclopentyloxy-3-methoxy)phenyl]vinyl}-3-(3,5-difluoro)phenyl-4H-pyrido[1,2-a]pyrimidin-4-one, 2-{(E)-2-[(2-Cyclopentyloxy-3-methoxy)phenyl]vinyl}-3-(3-trifluoromethyl)phenyl-4H-pyrido[1,2-a]pyrimidin-4-one, 2-{(E)-2-[2-(Cyclopentyloxy)-3-methoxyphenyl]vinyl}-3-(4-trifluoromethyl)phenyl-4H-pyrido[1,2-a]pyrimidin-4-one, 2-{(E)-2-[(2-Cyclopentyloxy-3-methoxy)phenyl]vinyl}-3-(4-trifluoromethoxy)phenyl-4H-pyrido[1,2-a]pyrimidin-4-one, 2-{(E)-2-[2-(Cyclopentyloxy)-3-methoxy)phenyl]vinyl}-3-(3-hydroxy)phenyl-4H-pyrido[1,2-a]-pyrimidin-4-one, 2-{(E)-2-[(2-Cyclopentyloxy-3-methoxy)phenyl]vinyl}-3-(3-methoxy)phenyl-4H-pyrido[1,2-a]pyrimidin-4-one, 3-(3-Isopropoxyphenyl)-2-[(E)-2-(2-cyclopentyloxy-3-methoxy)phenylvinyl]-4H-pyrido[1,2-a]pyrimidin-4-one, 4-{2-[(E)-2-(2-Cyclopentyloxy-3-methoxyphenyl)vinyl]-4-oxo-4H-pyrido[1,2-a]pyrimidin-3-yl}benzonitrile, 4-{4-Oxo-2-[(E)-2-(2-cyclopentyloxy-3-methoxy)phenylvinyl]-4H-pyrido[1,2-a]pyrimidin-3-yl}benzoic acid, 2-{(E)-2-[(2-Cyclopentyloxy)-3-methoxyphenyl]vinyl}-3-(4-nitro)phenyl-4H-pyrido[1,2-a]pyrimidin-4-one, N-(3-{2-[(E)-2-(2-Cyclopentyloxy-3-methoxy)phenylvinyl]-4-oxo-4H-pyrido[1,2-a]pyrimidin-3-yl}phenyl) acetamide, N-(4-{2-[(E)-2-(2-Cyclopentyloxy-3-methoxy)phenylvinyl]-4-Oxo-4H-pyrido[1,2-a]pyrimidin-3-yl}phenyl) acetamide, 3-(4-Acetylphenyl)-2-[(E)-2-(2-cyclopentyloxy-3-methoxy)phenylvinyl]-4H-pyrido[1,2-a]pyrimidin-4-one, 2-{(E)-2-[(2-Cyclopentyloxy-3-methoxy)phenyl]vinyl}-3-(4-thiomethyl)phenyl-4H-pyrido[1,2-a]pyrimidin-4-one, 2-{(E)-2-[2-(Cyclopentyloxy)-3-methoxyphenyl]vinyl}-3-pyridin-4-yl-4H-pyrido[1,2-a]-pyrimidin-4-one, 2-{(E)-2-[2-(Cyclopentyloxy)-3-methoxyphenyl]vinyl}-3-(6-fluoro)pyridin-3-yl-4H-pyrido[1,2-a]pyrimidin-4-one, 3-(1,3-Benzodioxol-5-yl)-2-[(E)-2-(2-cyclopentyloxy-3-methoxy)phenylvinyl]-4H-pyrido[1,2-a]pyrimidin-4-one, 2-[(E)-2-(2-Cyclopentyloxy-3-methoxyphenyl)vinyl]-3-(2,3-dihydro-1,4-benzodioxin-6-yl)-4H-pyrido[1,2-a]pyrimidin-4-one, 2-[(E)-2-(2-Cyclopentyloxy-3-methoxy)phenylvinyl]-3-quinolin-6-yl-4H-pyrido[1,2-a]pyrimidin-4-one, 2-{(E)-2-[(2-Cyclopentyloxy-3-methoxy)phenyl]vinyl}-9-methyl-3-(4-trifluoromethyl)phenyl-4H-pyrido[1,2-a]pyrimidin-4-one, 4-{2-[(E)-2-(2-Cyclopentyloxy-3-methoxyphenyl)vinyl]-9-methoxy-4-oxo-4H-pyrido[1,2-a]pyrimidin-3-yl}benzonitrile, 4-{7-Chloro-2-[(E)-2-[(2-Cyclopropylmethoxy-3-methoxyphenyl)vinyl]-4-oxo-4H-pyrido[1,2-a]pyrimidin-3-yl}benzonitrile and 4-{7-Chloro-2-[(E)-2-(2-cyclopentyloxy-3-methoxy)phenylvinyl]-4-oxo-4H-pyrido[1,2-a]pyrimidin-3-yl}benzonitrile or stereoisomer, enantiomer, diastereomer or pharmaceutically acceptable salt thereof.

23. A pharmaceutical composition comprising a compound according to claim 1, either as a free base or pharmaceutically acceptable salt form and a pharmaceutically acceptable excipient.

24. The pharmaceutical composition according to claim 23, wherein the pharmaceutically acceptable excipient is a carrier or diluent.

25. A compound selected from:

4-{2-[(E)-2-[3-Methoxy-2-pentyloxyphenyl)vinyl]-4-oxo-4H-pyrido[1,2-a]pyrimidin-3-yl}benzonitrile, 2-[(E)-2-[(2-Cyclopropylmethoxy-3-methoxyphenyl)vinyl]-3-[4-(trifluoromethyl)phenyl]-4H-pyrido[1,2-a]pyrimidin-4-one, 2-[(E)-2-[(2-Cyclopropylmethoxy-3-methoxyphenyl)vinyl]-3-[4-(trifluoro-methoxy)phenyl]-4H-pyrido[1,2-a]pyrimidin-4-one, 4-{2-[(E)-2-[(2-Cyclopropylmethoxy-3-methoxyphenyl)vinyl]-4-oxo-4H-pyrido[1,2-a]pyrimidin-3-yl}benzonitrile, 4-{2-[(E)-2-(2-Cyclopentyloxy-3-methoxyphenyl)vinyl]-4-oxo-4H-pyrido[1,2-a]pyrimidin-3-yl}benzonitrile, and 2-[(E)-2-(2-Cyclopentyloxy-3-methoxy)phenylvinyl]-3-quinolin-6-yl-4H-pyrido[1,2-a]pyrimidin-4-one or stereoisomer, enantiomer, diastereomer or pharmaceutically acceptable salt thereof.

\* \* \* \* \*

UNITED STATES PATENT AND TRADEMARK OFFICE
CERTIFICATE OF CORRECTION

PATENT NO. : 8,349,846 B2  
APPLICATION NO. : 12/811975  
DATED : January 8, 2013  
INVENTOR(S) : V S Prasadarao Lingam et al.

It is certified that error appears in the above-identified patent and that said Letters Patent is hereby corrected as shown below:

In the Specification

Column 1  
Lines 6-11, delete the entire paragraph and substitute the following:

--This application is a National Stage Application under 35 U.S.C. 371 of PCT International Application No. PCT/IN2009/000025, filed January 7, 2009, which claims the benefit of Indian Patent Application Nos. 82/MUM/2008 filed on January 11, 2008, 548/MUM/2008 filed on March 18, 2008, and 798/MUM/2008 filed on April 4, 2008, and U.S. Provisional Application Nos. 61/028,770, filed on February 14, 2008, and 61/048,276, filed on April 28, 2008, all of which are hereby incorporated by reference--.

Signed and Sealed this  
Eighth Day of July, 2014

Michelle K. Lee  
*Deputy Director of the United States Patent and Trademark Office*